United States Patent
Ben-David et al.

(10) Patent No.: US 8,060,197 B2
(45) Date of Patent: Nov. 15, 2011

(54) PARASYMPATHETIC STIMULATION FOR TERMINATION OF NON-SINUS ATRIAL TACHYCARDIA

(75) Inventors: Tamir Ben-David, Tel Aviv (IL); Omry Ben-Ezra, Tel Aviv (IL); Ehud Cohen, Ganei Tikva (IL)

(73) Assignee: Bio Control Medical (B.C.M.) Ltd., Yehud (IL)

( * ) Notice: Subject to any disclaimer, the term of this patent is extended or adjusted under 35 U.S.C. 154(b) by 181 days.

(21) Appl. No.: 11/724,899

(22) Filed: Mar. 16, 2007

(65) Prior Publication Data

US 2007/0203527 A1    Aug. 30, 2007

Related U.S. Application Data

(63) Continuation-in-part of application No. 10/560,654, filed as application No. PCT/IL2004/000496 on Jun. 10, 2004, and a continuation-in-part of application No. 10/461,696, filed on Jun. 13, 2003, now Pat. No. 7,321,793, application No. 11/724,899, which is a continuation-in-part of application No. 11/657,784, filed on Jan. 24, 2007, which is a continuation-in-part of application No. 10/866,601, filed on Jun. 10, 2004, said application No. 11/657,784 is a continuation-in-part of application No. 11/234,877, filed on Sep. 22, 2005, which is a continuation-in-part of application No. 11/064,446, filed on Feb. 22, 2005, which is a continuation-in-part of application No. 11/062,324, filed on Feb. 18, 2005, which is a continuation-in-part of application No. 10/719,659, filed on Nov. 20, 2003, which is a continuation-in-part of application No. PCT/IL03/00431, filed on May 23, 2003, said application No. 11/234,877 is a continuation-in-part of application No. 10/560,654, filed as application No. PCT/IL2004/000496 on Jun. 10, 2004, which is a continuation-in-part of application No. 10/461,696, filed on Jun. 13, 2003, now Pat. No. 7,321,793, said application No. 11/657,784 is a continuation-in-part of application No. 11/359,266, filed on Feb. 21, 2006, and a continuation-in-part of application No. 10/866,601, filed on Jun. 10, 2004.

(60) Provisional application No. 60/478,576, filed on Jun. 13, 2003, provisional application No. 60/612,428, filed on Sep. 23, 2004, provisional application No. 60/668,275, filed on Apr. 4, 2005, provisional application No. 60/655,604, filed on Feb. 22, 2005.

(51) Int. Cl.
   *A61N 1/37* (2006.01)
(52) U.S. Cl. .................. 607/5; 607/7; 607/9; 607/14
(58) Field of Classification Search .................. 607/5, 7, 607/9, 14, 16
   See application file for complete search history.

(56) References Cited

U.S. PATENT DOCUMENTS 3,411,507 A    11/1968    Wingrove
(Continued)

FOREIGN PATENT DOCUMENTS

EP    0688577    12/1995
(Continued)

OTHER PUBLICATIONS

Y. Zhang, et al., (2002) "Optimal Ventricular Rate Slowing During Atrial Fibrillation by Feedback AV Nodal-Selective Vagal Stimulation," *Am J Physiol Heart Circ*, Physiol 282: H1102-H1110.

(Continued)

*Primary Examiner* — Scott Getzow
*Assistant Examiner* — Joseph Dietrich
(74) *Attorney, Agent, or Firm* — Sughrue Mion, PLLC

(57) ABSTRACT

Apparatus is provided, which includes an electrode device, configured to be coupled to an atrial site of a subject containing parasympathetic nervous tissue, and a control unit. The control unit is configured to, responsively to a detection of an episode of non-sinus atrial tachycardia, restore normal sinus rhythm (NSR) of the subject, by driving the electrode device to apply a parasympathetic stimulation signal to the atrial site, and configuring the parasympathetic stimulation signal to activate the parasympathetic nervous tissue sufficiently to restore the NSR. Other embodiments are also described.

41 Claims, 7 Drawing Sheets

U.S. PATENT DOCUMENTS

| | | | |
|---|---|---|---|
| 4,019,518 A | 4/1977 | Maurer et al. |
| 4,161,952 A | 7/1979 | Kinney et al. |
| 4,338,945 A | 7/1982 | Kosugi et al. |
| 4,392,496 A | 7/1983 | Stanton |
| 4,535,785 A | 8/1985 | Van Den Honert |
| 4,559,948 A | 12/1985 | Liss et al. |
| 4,573,481 A | 3/1986 | Bullara |
| 4,585,005 A | 4/1986 | Lue et al. |
| 4,602,624 A | 7/1986 | Naples et al. |
| 4,608,985 A | 9/1986 | Crish et al. |
| 4,628,942 A | 12/1986 | Sweeney et al. |
| 4,632,116 A | 12/1986 | Rosen |
| 4,649,936 A | 3/1987 | Ungar et al. |
| 4,663,102 A | 5/1987 | Brenman et al. |
| 4,702,254 A | 10/1987 | Zabara |
| 4,739,764 A | 4/1988 | Lue et al. |
| 4,867,164 A | 9/1989 | Zabara |
| 4,926,865 A | 5/1990 | Oman |
| 4,962,751 A | 10/1990 | Krauter |
| 5,025,807 A | 6/1991 | Zabara |
| 5,042,497 A | 8/1991 | Shapland |
| 5,069,680 A | 12/1991 | Grandjean |
| 5,170,802 A | 12/1992 | Mehra |
| 5,178,161 A | 1/1993 | Kovacs |
| 5,188,104 A | 2/1993 | Wernicke et al. |
| 5,199,428 A | 4/1993 | Obel et al. |
| 5,199,430 A | 4/1993 | Fang et al. |
| 5,203,326 A | 4/1993 | Collins |
| 5,205,285 A | 4/1993 | Baker |
| 5,215,086 A | 6/1993 | Terry et al. |
| 5,224,491 A | 7/1993 | Mehra |
| 5,243,980 A | 9/1993 | Mehra |
| 5,263,480 A | 11/1993 | Wernicke et al. |
| 5,282,468 A | 2/1994 | Klepinski |
| 5,292,344 A | 3/1994 | Douglas |
| 5,299,569 A | 4/1994 | Wernicke et al. |
| 5,314,495 A | 5/1994 | Kovacs |
| 5,330,507 A | 7/1994 | Schwartz |
| 5,334,221 A | 8/1994 | Bardy |
| 5,335,657 A | 8/1994 | Terry et al. |
| 5,356,425 A | 10/1994 | Bardy et al. |
| 5,411,531 A | 5/1995 | Hill et al. |
| 5,423,872 A | 6/1995 | Cigaina |
| 5,437,285 A | 8/1995 | Verrier et al. |
| 5,439,938 A | 8/1995 | Snyder et al. |
| 5,454,840 A | 10/1995 | Krakovsky et al. |
| 5,487,756 A | 1/1996 | Kallesoe et al. |
| 5,507,784 A | 4/1996 | Hill et al. |
| 5,522,854 A | 6/1996 | Ideker et al. |
| 5,540,730 A | 7/1996 | Terry et al. |
| 5,540,734 A | 7/1996 | Zabara |
| 5,562,595 A * | 10/1996 | Neisz ............................ 607/5 |
| 5,562,718 A | 10/1996 | Palermo |
| 5,571,150 A | 11/1996 | Wernicke et al. |
| 5,578,061 A | 11/1996 | Stroemann et al. |
| 5,628,777 A | 5/1997 | Moberg et al. |
| 5,634,462 A | 6/1997 | Tyler et al. |
| 5,645,570 A | 7/1997 | Corbucci |
| 5,658,318 A | 8/1997 | Stroetmann et al. |
| 5,690,681 A | 11/1997 | Geddes et al. |
| 5,690,691 A | 11/1997 | Chen |
| 5,700,282 A | 12/1997 | Zabara |
| 5,707,400 A | 1/1998 | Terry et al. |
| 5,711,316 A | 1/1998 | Elsberry et al. |
| 5,716,385 A | 2/1998 | Mittal et al. |
| 5,755,750 A | 5/1998 | Petruska et al. |
| 5,824,027 A | 10/1998 | Hoffer et al. |
| 5,832,932 A | 11/1998 | Elsberry et al. |
| 5,833,709 A | 11/1998 | Rise et al. |
| 5,836,994 A | 11/1998 | Bourgeois |
| 5,916,239 A | 6/1999 | Geddes et al. |
| 5,938,584 A | 8/1999 | Ardito et al. |
| 5,938,596 A | 8/1999 | Woloszko et al. |
| 6,006,134 A | 12/1999 | Hill et al. |
| 6,026,326 A | 2/2000 | Bardy |
| 6,058,331 A | 5/2000 | King et al. |
| 6,066,163 A | 5/2000 | John |
| 6,073,048 A | 6/2000 | Kieval et al. |
| 6,086,525 A | 7/2000 | Davey et al. |
| 6,091,977 A | 7/2000 | Tarjan et al. |
| 6,091,992 A | 7/2000 | Bourgeois |
| 6,094,598 A | 7/2000 | Elsberry et al. |
| 6,097,984 A | 8/2000 | Douglas |
| 6,104,955 A | 8/2000 | Bourgeois |
| 6,104,960 A | 8/2000 | Duysens et al. |
| 6,119,516 A | 9/2000 | Hock |
| 6,134,470 A | 10/2000 | Hartlaub |
| 6,146,335 A | 11/2000 | Gozani |
| 6,161,029 A | 12/2000 | Spreigl et al. |
| 6,167,304 A | 12/2000 | Loos |
| 6,169,924 B1 | 1/2001 | Meloy et al. |
| 6,205,359 B1 | 3/2001 | Boveja |
| 6,230,061 B1 | 5/2001 | Hartung |
| 6,240,314 B1 | 5/2001 | Plicchi et al. |
| 6,266,564 B1 | 7/2001 | Hill |
| 6,272,377 B1 | 8/2001 | Sweeney et al. |
| 6,292,695 B1 | 9/2001 | Webster et al. |
| 6,319,241 B1 | 11/2001 | King et al. |
| 6,341,236 B1 | 1/2002 | Osorio et al. |
| 6,356,784 B1 | 3/2002 | Lozano et al. |
| 6,366,813 B1 | 4/2002 | DiLorenzo |
| 6,381,499 B1 | 4/2002 | Taylor et al. |
| 6,400,982 B2 | 6/2002 | Sweeney et al. |
| 6,405,079 B1 | 6/2002 | Ansarinia |
| 6,434,424 B1 | 8/2002 | Igel et al. |
| 6,449,507 B1 | 9/2002 | Hill et al. |
| 6,456,866 B1 | 9/2002 | Tyler et al. |
| 6,463,328 B1 | 10/2002 | John |
| 6,473,644 B1 | 10/2002 | Terry et al. |
| 6,477,406 B1 * | 11/2002 | Turcott ............................ 607/36 |
| 6,493,585 B2 | 12/2002 | Plicchi et al. |
| 6,511,500 B1 | 1/2003 | Rahme |
| 6,542,774 B2 | 4/2003 | Hill et al. |
| 6,564,096 B2 | 5/2003 | Mest |
| 6,587,727 B2 | 7/2003 | Osorio et al. |
| 6,600,956 B2 | 7/2003 | Maschino et al. |
| 6,610,713 B2 | 8/2003 | Tracey |
| 6,611,713 B2 | 8/2003 | Schauerte |
| 6,622,041 B2 | 9/2003 | Terry et al. |
| 6,628,987 B1 | 9/2003 | Hill et al. |
| 6,668,191 B1 | 12/2003 | Boveja |
| 6,671,556 B2 | 12/2003 | Osorio et al. |
| 6,684,105 B2 | 1/2004 | Cohen et al. |
| RE38,705 E | 2/2005 | Hill et al. |
| 6,865,416 B2 | 3/2005 | Dev et al. |
| 6,895,280 B2 | 5/2005 | Meadows et al. |
| 6,907,295 B2 | 6/2005 | Gross et al. |
| 6,920,357 B2 | 7/2005 | Osorio et al. |
| 6,928,320 B2 | 8/2005 | King |
| 6,934,583 B2 | 8/2005 | Weinberg et al. |
| 6,961,618 B2 | 11/2005 | Osorio et al. |
| 6,985,774 B2 | 1/2006 | Kieval et al. |
| 7,050,846 B2 | 5/2006 | Sweeney et al. |
| 7,058,447 B2 | 6/2006 | Hill et al. |
| 7,076,299 B2 | 7/2006 | Thong |
| 7,142,917 B2 | 11/2006 | Fukui |
| 7,149,574 B2 | 12/2006 | Yun et al. |
| 7,269,457 B2 | 9/2007 | Shafer et al. |
| 7,277,752 B2 | 10/2007 | Matos |
| 7,277,761 B2 | 10/2007 | Shelchuk |
| 7,282,030 B2 | 10/2007 | Frei et al. |
| 7,292,890 B2 | 11/2007 | Whitehurst et al. |
| 7,333,858 B2 | 2/2008 | Killian et al. |
| 7,336,997 B2 | 2/2008 | Fukui |
| 7,346,398 B2 | 3/2008 | Gross et al. |
| 7,403,819 B1 | 7/2008 | Shelchuk et al. |
| 7,460,906 B2 | 12/2008 | Libbus |
| 7,623,926 B2 | 11/2009 | Rossing et al. |
| 7,765,000 B2 | 7/2010 | Zhang et al. |
| 2002/0107553 A1 | 8/2002 | Hill et al. |
| 2003/0018367 A1 | 1/2003 | Dilorenzo |
| 2003/0045909 A1 | 3/2003 | Gross et al. |
| 2003/0100924 A1 | 5/2003 | Foreman et al. |
| 2003/0229380 A1 | 12/2003 | Adams et al. |
| 2004/0048795 A1 | 3/2004 | Ivanova et al. |
| 2004/0059392 A1 | 3/2004 | Parramon et al. |
| 2004/0138721 A1 | 7/2004 | Osorio et al. |

| | | | |
|---|---|---|---|
| 2004/0158119 A1 | 8/2004 | Osorio et al. | |
| 2004/0243182 A1 | 12/2004 | Cohen et al. | |
| 2005/0131467 A1 | 6/2005 | Boveja | |
| 2005/0187584 A1 | 8/2005 | Denker et al. | |
| 2006/0015153 A1 | 1/2006 | Gliner et al. | |
| 2006/0030919 A1 | 2/2006 | Mrva et al. | |
| 2006/0074450 A1 | 4/2006 | Boveja | |
| 2006/0129205 A1 | 6/2006 | Boveja et al. | |
| 2006/0136024 A1 | 6/2006 | Cohen et al. | |
| 2006/0195170 A1 | 8/2006 | Cohen et al. | |
| 2006/0282145 A1 | 12/2006 | Caparso et al. | |
| 2008/0228238 A1 | 9/2008 | Libbus | |
| 2008/0234780 A1 | 9/2008 | Smith et al. | |

FOREIGN PATENT DOCUMENTS

| | | |
|---|---|---|
| EP | 0831954 | 3/2004 |
| WO | WO 0110375 | 2/2001 |
| WO | WO 0110432 | 2/2001 |
| WO | WO 0126729 | 4/2001 |
| WO | WO 02085448 | 10/2002 |

OTHER PUBLICATIONS

N.J.M. Rijkhoff, et al., (1999) "Selective Stimulation of Small Diameter Nerve Fibers in a Mixed Bundle", *Proceedings of the Annual Project Meeting Sensations/Neuros and Mid Term Review Meeting Neuros*, Apr. 21-23.

M. Manfredi,(1970) "Differential Block of Conduction of Large Fibers in Peripheral Nerve by Direct Current", *Arch. Ital. Biol.* 108: 52-71.

Fuster and Ryden, et al., (2001) "ACC/AHA/ESC Practice Guidelines" *JACC*, vol. 38: No. 4.

Bilgutay, et al., (1968) "Vagal Tuning: A New Concept in the Treatment of Supraventricular Arrhythmias, Angina Pectoris, and Heart Failure", *J. Thoracic Cardiovasc. Surg.*, 56(1): 71-82, July.

Gregory S. Friedrichs, (2000) "Experimental Models of Atrial Fibrillation/Flutter", *Journal of Pharmacological and Toxicological Methods*, 43: 117-123.

Ake Hjalmarson, (1999) "Prevention of Sudden Cardiac Death with Beta Blockers", *Clin. Cardiol. 22*, (Suppl. V): V11-V15.

Danshi Li, et al., (1999) "Promotion of Atrial Fibrillation by Heart Failure in Dogs", *Circulation*, Jul. 6: 87-95.

Herman Kwan, et al., (2001) "Cardiovascular Adverse Drug Reactions During Initiation of Antiarrhythmic Therapy for Atrial Fibrillayion", *Can J Hosp Pharm*, vol. 54: 10-14.

Lena Jideus, (2001) "Atrial Fibrillation After Coronary Artery Bypass Surgery", *Acta Universitatis Upsaliensis*, Uppsala.

Cummings JE, et al., (2004) "Preservation of the Anterior Fat Pad Paradoxically Decreases the Incidence of Postoperative Atrial Fibrillation in Humans", *Journal of the American College Cardiology*, 43(6):994-1000.

Carlson MD, et al., (1992) "Selective Stimulation of Parasympathetic Nerve Fibers to the Human Sinoatrial Node", *Circulation*, 85: 1311-1317.

Pagé PL, et al., (1995) "Regional Distribution of Atrial Electrical Changes Induced by Stimulation of Extracardiac and Intracardiac Neural Elements", *The Journal of Thoracic and Cardiovascular Surgery*, 109(2): 377-388.

Mazgalev TN, "AV Nodal Physiology", *Heart Rhythm Society*, (www.hrsonline.org), no date.

Furukawa Y, et al., (1989) "Differential Blocking Effects of Atropine and Gallamine on Negative Chronotropic and Dromotropic Responses to Vagus Stimulation in Anesthetized Dogs", *Journal of Pharmacology and Experimental Therapeutics*, 251(3): 797-802.

Bluemel KM, (1990) "Parasympathetic Postganglionic Pathways to the Sinoatrial Node", *J Physiol*. 259(5 Pt 2): H1504-H1510.

Bibevski S, et al., (1999) "Ganglionic Mehanisms Contribute to Diminished Vagal Control in Heart Failure", *Circulation*, 99: 2958-2963.

Garrigue S, et al., (1998) "Post-ganglionic Vagal Stimulation of the Atrioventricular Node Reduces ventricular Rate During Atrial Fibrillation", *PACE*, 21(4): Part II, 878.

Chen SA, et al., (1998) "Intracardiac Stimulation of Human Parasympathetic Nerve Fibers Induces Negative Dromotropic effects: Implication with the Lesions of Radiofrequency Catheter Ablation", *J Cardiovasc Electrophysiol.*, 9(3): 245-252.

Goldberger JJ, et al., (1999) "New Technique for Vagal Nerve Stimulation", *Journal of Neuroscience Methods*, 91(1-2): 109-114.

Cooper, et al., (1980) "Neural Effects on Sinus Rate and Atrial Ventricular Conduction Produced by Electrical Stimulation from a Transvenous Electrode catheter in the Canine right Pulmonary Artery", *Circulation Research*, 46(1): 48-57.

Waninger MS, et al., (2000) "Electrophysiological Control of Ventricualr Rate During Atrial Fibrillation", *PACE*, 23:1239-1244.

N.J.M. Rijkhoff, et al., (1998) "Orderly Recruitment of Motoneurons in an Acute Rabbit Model", *Proc. of the 20th Annual Int. Conf for the IEEE Engineering in Medicine and Biology Society*, 20(5).

D.M. Fitzpatrick, et al., (1991) "A Nerve Cuff Design for the Selective Activation and Blocking of Myelinated Nerve Fibers", *Annual Int. Conf. of the IEEE Eng. In Medicine and Biology Society*, 13(2).

Walter C. Randall, (1977) "Neural Regulation of the Heart", New York, Oxford University Press.

U.S. Statutory Invention Registration No. H1,905; published Oct. 3, 2000 (Hill).

Office Action, issued Jun. 15, 2009, in connection with U.S. Appl. No. 11/064,446, filed Feb. 22, 2005.

Office Action issued Jun. 24, 2009, in connection U.S. Appl. No. 11/978,379, filed Oct. 29, 2007.

Office Action, issued Aug. 21, 2009, in connection with U.S. Appl. No. 11/975,240, filed Oct. 17, 2007.

Morillo et al., "Chronic Rapid Atrial Pacing. Structural functional, and electrophysiological characteristics of a new model of sustained atrial fibrillation," *Circulation*, 1995, 91(5), 1588-1595.

Office Action, issued Feb. 5, 2010, in connection with U.S. Appl. No. 11/974,951, filed Oct. 16, 2007.

Office Action, issued Apr. 6, 2010, in connection with U.S. Appl. No. 11/977,291, filed Oct. 23, 2007.

An Official Action dated Feb. 4, 2011, which issued during the prosecution of Applicant's U.S. Appl. No. 11/974,951.

An Official Action dated May 26, 2011, which issued during the prosecution of Applicant's U.S. Appl. No. 12/012,366.

* cited by examiner

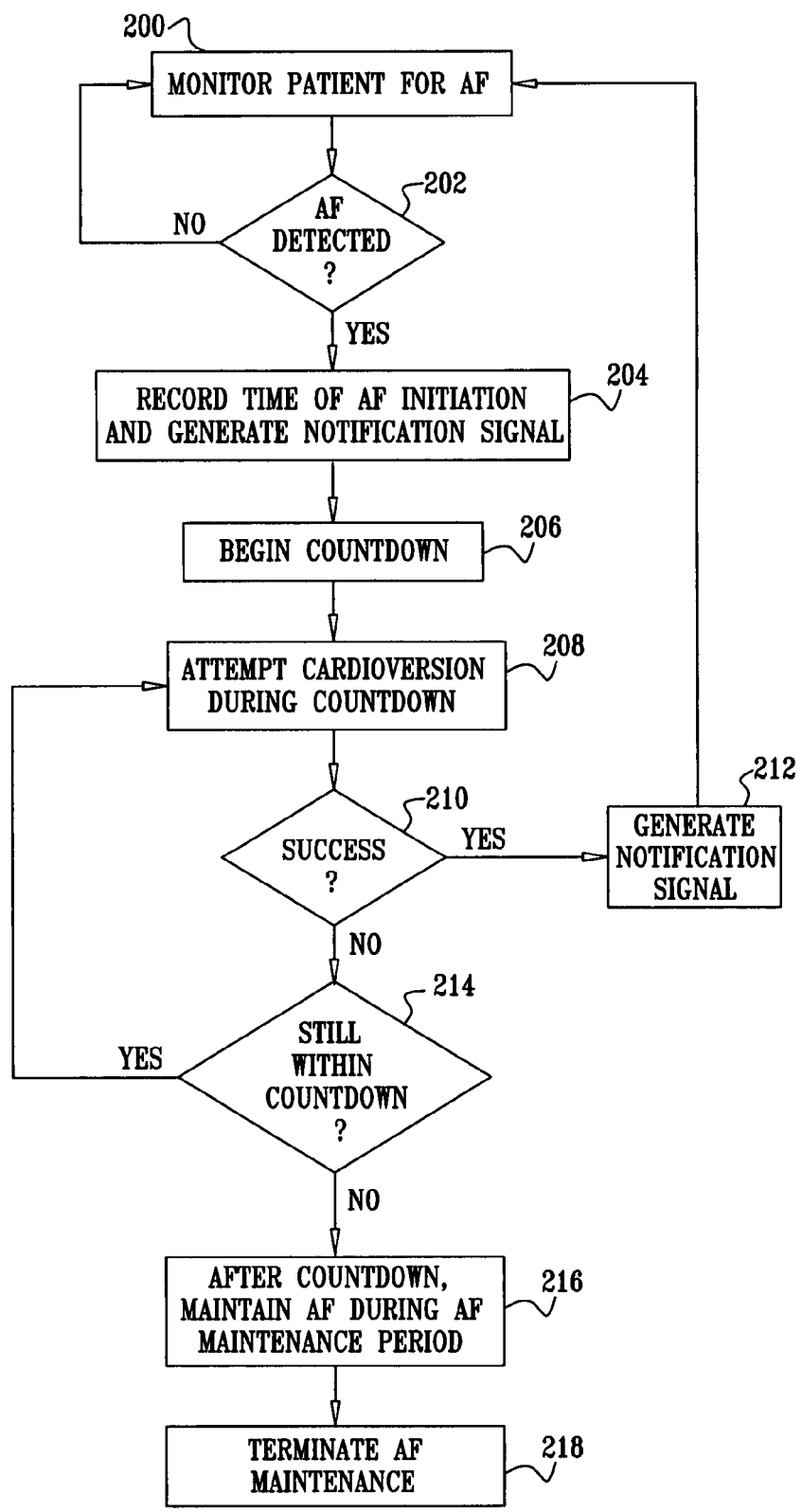

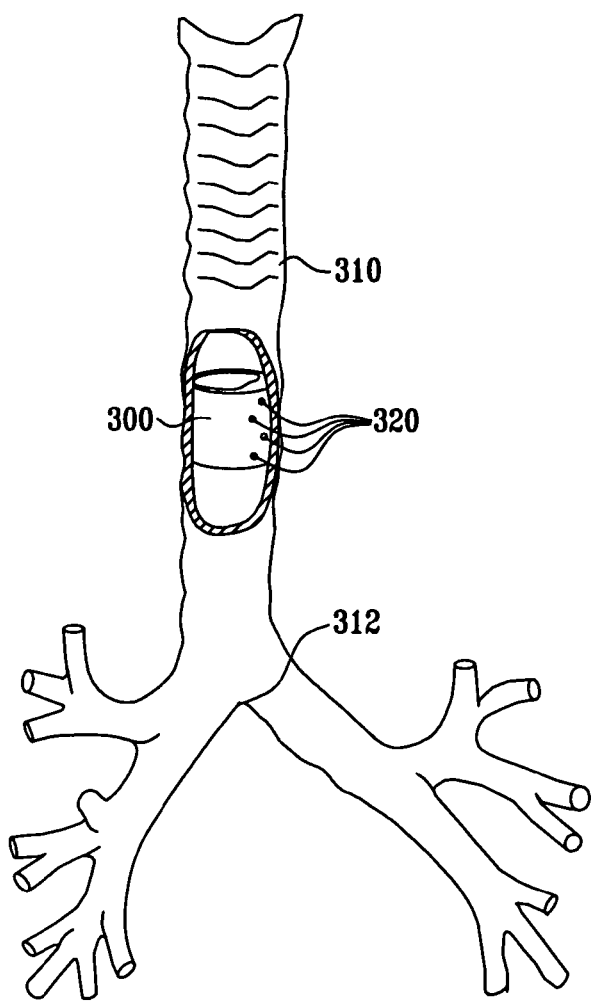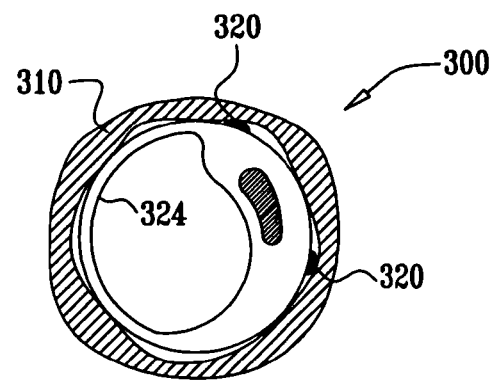

PARASYMPATHETIC STIMULATION FOR TERMINATION OF NON-SINUS ATRIAL TACHYCARDIA

CROSS-REFERENCES TO RELATED APPLICATIONS

This application is a continuation-in-part of:
(a) U.S. Ser. No. 10/560,654, filed May 1, 2006, which is the §371 National Stage of PCT International Application No. PCT/IL2004/00496, filed Jun. 10, 2004, which: (i) is a continuation-in-part of U.S. Ser. No. 10/461,696, filed Jun. 13, 2003, now U.S. Pat. No. 7,321,793 and (ii) claims the benefit of U.S. Provisional Application No. 60/478,576, filed Jun. 13, 2003; and
(b) U.S. Ser. No. 11/657,784, filed Jan. 24, 2007, which is a continuation-in-part of:
  (i) U.S. Ser. No. 10/866,601, filed Jun. 10, 2004, which claims the benefit of U.S. Provisional Application No. 60/478,576, filed Jun. 13, 2003;
  (ii) U.S. Ser. No. 11/234,877, filed Sep. 22, 2005, which:
    (1) is a continuation-in-part of U.S. Ser. No. 11/064,446, filed Feb. 22, 2005, which is a continuation-in-part of U.S. Ser. No. 11/062,324, filed Feb. 18, 2005, which is a continuation-in-part of U.S. Ser. No. 10/719,659, filed Nov. 20, 2003, which is a continuation-in-part of PCT International Application No. PCT/IL2003/00431, filed May 23, 2003;
    (2) claims the benefit of:
      (i) U.S. Provisional Application No. 60/612,428, filed Sep. 23, 2004; and
      (ii) U.S. Provisional Application No. 60/668,275, filed Apr. 4, 2005;
    (iii) U.S. Ser. No. 10/560,654, filed May 1, 2006, which is the §371 National Stage of PCT International Application No. PCT/IL2004/00496, filed Jun. 10, 2004, which is a continuation-in-part of U.S. Ser. No. 10/461,696, filed Jun. 13, 2003, now U.S. Pat. No. 7,321,793; and
    (iv) U.S. Ser. No. 11/359,266, filed Feb. 21, 2006, which: (1) claims the benefit of U.S. Provisional Application No. 60/655,604, filed Feb. 22, 2005, and (2) is a continuation-in-part of U.S. Ser. No. 10/866,601, filed Jun. 10, 2004, the contents of each of which is hereby incorporated by reference herein.

FIELD OF THE INVENTION

The present invention relates generally to treating patients by application of electrical signals to selected tissue, and specifically to methods and apparatus for stimulating tissue for treating patients suffering from non-sinus atrial tachycardia and other conditions.

BACKGROUND OF THE INVENTION

The use of nerve stimulation for treating and controlling a variety of medical, psychiatric, and neurological disorders has seen significant growth over the last several decades, including for treatment of heart conditions. In particular, stimulation of the vagus nerve (the tenth cranial nerve, and part of the parasympathetic nervous system) has been the subject of considerable research. The vagus nerve is composed of somatic and visceral afferents (inward conducting nerve fibers, which convey impulses toward the brain) and efferents (outward conducting nerve fibers, which convey impulses to an effector to regulate activity such as muscle contraction or glandular secretion).

The rate of the heart is restrained in part by parasympathetic stimulation from the right and left vagus nerves. Low vagal nerve activity is considered to be related to various arrhythmias, including tachycardia, ventricular accelerated rhythm, and rapid atrial fibrillation. Stimulation of the vagus nerve has been proposed as a method for treating various heart conditions, including atrial fibrillation and heart failure. By artificially stimulating the vagus nerves, it is possible to slow the heart, allowing the heart to more completely relax and the ventricles to experience increased filling. With larger diastolic volumes, the heart may beat more efficiently because it may expend less energy to overcome the myocardial viscosity and elastic forces of the heart with each beat.

Atrial fibrillation is a condition in which the atria of the heart fail to continuously contract in synchrony with the ventricles of the heart. During fibrillation, the atria undergo rapid and unorganized electrical depolarization, so that no contractile force is produced. The ventricles, which normally receive contraction signals from the atria (through the atrioventricular (AV) node), are inundated with signals, typically resulting in a rapid and irregular ventricular rate. Because of this rapid and irregular rate, the patient suffers from reduced cardiac output, a feeling of palpitations, and/or increased risk of thromboembolic events.

Current therapy for atrial fibrillation includes cardioversion and rate control. Cardioversion is the conversion of the abnormal atrial rhythm into normal sinus rhythm. This conversion is generally achieved pharmacologically or electrically. An atrial defibrillator applies an electrical shock when an episode of arrhythmia is detected. Such a device has not shown widespread clinical applicability because of the pain that is often associated with such electrical shocks. Atrial override pacing (the delivery of rapid atrial pacing to override abnormal atrial rhythms) has not shown sufficient clinical benefit to justify clinical use. Rate control therapy is used to control the ventricular rate, while allowing the atria to continue fibrillation. This is generally achieved by slowing the conduction of signals through the AV node from the atria to the ventricles.

Current treatment techniques have generally not demonstrated long-term efficacy in preventing the recurrence of episodes of atrial fibrillation. Because of the high frequency of recurrences (up to several times each day), and a lack of effective preventive measures, many patients live in a constant state of atrial arrhythmia, which is associated with increased morbidity and mortality.

European Patent Application EP 0 688 577 to Holmström et al., which is incorporated herein by reference, describes a device for supraventricular heart therapy. The device contains an arrhythmia detector for detecting supraventricular arrhythmia and a nerve stimulator for emitting pulses, in response to the detection, to a physiological representative of the parasympathetic nervous system via an electrode system. The electrode system comprises means stimulation means devised to be placeable in an extracardiac position in the neck area of the physiological representative of the parasympathetic nervous system, and for activating this nervous system in direct contact therewith, or via an adjacent blood vessel.

Bilgutay et al., in "Vagal tuning: a new concept in the treatment of supraventricular arrhythmias, angina pectoris, and heart failure," J. Thoracic Cardiovas. Surg. 56(1):71-82, July, 1968, which is incorporated herein by reference, studied the use of a permanently-implanted device with electrodes to stimulate the right vagus nerve for treatment of supraventricular arrhythmias, angina pectoris, and heart failure.

Experiments were conducted to determine amplitudes, frequencies, wave shapes and pulse lengths of the stimulating current to achieve slowing of the heart rate. The authors additionally studied an external device, triggered by the R-wave of the electrocardiogram (ECG) of the subject to provide stimulation only upon an achievement of a certain heart rate. They found that when a pulsatile current with a frequency of ten pulses per second and 0.2 milliseconds pulse duration was applied to the vagus nerve, the heart rate could be decreased to half the resting rate while still preserving sinus rhythm. Low amplitude vagal stimulation was employed to control induced tachycardias and ectopic beats.

U.S. Pat. No. 6,934,583 to Weinberg et al., which is incorporated herein by reference, describes techniques for stimulating the right vagal nerve within a living body via positioning an electrode portion of a lead proximate to the portion of the vagus nerve where the right cardiac branch is located and delivering an electrical signal to an electrode portion adapted to be implanted therein. Stimulation of the right vagus nerve and/or the cardiac branch thereof act to slow the atrial heart rate. Exemplary embodiments include deploying an expandable or self-oriented electrode. Various dedicated and single-pass leads are disclosed, as well as, various electrodes, and stabilization means. The methods include preserving sinus rhythm, avoiding asystole, preserving A-V synchrony, automatically determining parameter combinations that achieve these features, and further (in one embodiment) automatically determining parameter combinations achieve these features and reduce current drain.

Schaldach M, in "New concepts in electrotherapy of the heart," *Electrotherapy of the heart*, Springer Verlag Heidelberg, pp. 210-214 (1992), which is incorporated herein by reference, writes that "a general concept of electrical treatment of arrhythmia becomes possible if the neural factors in the arrhythmogenesis are considered. With the powerful tool of monitoring the sympathetic tone by intraventricular impedance measurements, the VIP that was introduced for the restoration of chronotropy will serve as a sensor of the increased neural activity of an impending arrhythmia, therefore making it possible to prevent tachycardia" (p. 210, emphasis in the original).

U.S. Pat. No. 5,318,592 to Schaldach, which is incorporated herein by reference, describes a cardiac therapy system for use with a conventional cardiac pacemaker is controlled by activity signals of the autonomous nervous system (ANS) in a patient's body which constitute a measure for the patient's cardiovascular output requirement. The system includes pickup circuitry for detecting at least the autonomous nervous system activity signals in the patient's body, a control circuit for generating control signals as a function of time and/or intensity of the autonomous nervous system signals picked up in the patient's body, a neurostimulator for changing vascular resistance by nerve stimulation of the patient in adaptation to the patient's intracardial output requirement, in response to control signals from the control circuit, an arrhythmia suppressor for generating anti-arrhythmia stimulation pulses to the patient's heart which are controlled by control signals from the control circuit, and a pump assist for assisting the pumping of the patient's heart in response to control signals from the control circuit.

U.S. Pat. No. 5,203,326 to Collins, which is incorporated herein by reference, describes a pacemaker which detects a cardiac abnormality and responds with electrical stimulation of the heart combined with vagus nerve stimulation. The vagal stimulation frequency is progressively increased in one-minute intervals, and, for the pulse delivery rate selected, the heart rate is described as being slowed to a desired, stable level by increasing the pulse current.

Moreira et al., in "Chronic rapid atrial pacing to maintain atrial fibrillation: Use to permit control of ventricular rate in order to treat tachycardia induced cardiomyopathy," Pacing Clin Electrophysiol, 12(5):761-775 (May 1989), which is incorporated herein by reference, describe the acute induction of atrial fibrillation with rapid atrial pacing, and an associated reduction in ventricular rate with digitalis therapy. Different treatment protocols are described to induce and maintain atrial fibrillation, in order to bring a patient with NYHA class III-IV congestive heart failure to a more moderate NYHA class II.

Preston et al., in "Permanent rapid atrial pacing to control supraventricular tachycardia," Pacing Clin Electrophysiol, 2(3):331-334 (May 1979), which is incorporated herein by reference, describe a patient who had continuous supraventricular tachycardia with a ventricular rate of about 170. The arrhythmia was refractory to drugs and DC countershock, and did not convert with atrial pacing. Rapid atrial stimulation (pacing at 300-400/min) controlled the ventricular rate by simulating atrial fibrillation. This therapy was used on a permanent basis for more than five months.

PCT Publication WO 04/110550 to Ben-Ezra et al., which is assigned to the assignee of the present application and is incorporated herein by reference, describes apparatus for treating a subject suffering from spontaneous atrial fibrillation, including an electrode device, adapted to be coupled to a site of the subject selected from the list consisting of: a vagus nerve, an epicardial fat pad, a pulmonary vein, a carotid artery, a carotid sinus, a vena cava vein, and an internal jugular vein, and a control unit, adapted to drive the electrode device to apply an electrical current to the site, and to configure the current to maintain the spontaneous AF for at least about 24 hours, so as to modify blood flow within the atria and reduce risk of thromboembolic events. In other embodiments, the control unit drives an electrode device to apply signals to the vagus nerve, and configures the signals so as to restore NSR, i.e., to induce cardioversion. According to one approach for restoring NSR, the configuration includes repeatedly changing parameters of the stimulation.

The following articles, which are incorporated herein by reference, may be of interest:

Goldberger J J et al., "New technique for vagal nerve stimulation," J Neurosci Methods 91(1-2):109-14 (1999)

Zhang Y et al., "Optimal ventricular rate slowing during atrial fibrillation by feedback AV nodal-selective vagal stimulation," Am J Physiol Heart Circ Physiol 282:H1102-H1110 (2002)

Martin P J et al., "Phasic effects of repetitive vagal stimulation on atrial contraction," Circ. Res. 52(6):657-63 (1983)

Wallick D W et al., "Effects of repetitive bursts of vagal activity on atrioventricular junctional rate in dogs," Am J Physiol 237(3):H275-81 (1979)

Morady F et al., "Effects of resting vagal tone on accessory atrioventricular connections," Circulation 81(1):86-90 (1990)

Waninger M S et al., "Electrophysiological control of ventricular rate during atrial fibrillation," PACE 23:1239-1244 (2000)

Wijffels M C et al., "Atrial fibrillation begets atrial fibrillation," Circulation 92:1954-1968 (1995)

Goldberger A L et al., "Vagally-mediated atrial fibrillation in dogs: conversion with bretylium tosylate," Int J Cardiol 13(1):47-55 (1986)

Takei M et al., "Vagal stimulation prior to atrial rapid pacing protects the atrium from electrical remodeling in anesthetized dogs," Jpn Circ J 65(12):1077-81 (2001)

Friedrichs G S, "Experimental models of atrial fibrillation/flutter," J Pharmacological and Toxicological Methods 43:117-123 (2000)

Hayashi H et al., "Different effects of class Ic and III antiarrhythmic drugs on vagotonic atrial fibrillation in the canine heart," Journal of Cardiovascular Pharmacology 31:101-107 (1998)

Morillo C A et al., "Chronic rapid atrial pacing. Structural, functional, and electrophysiological characteristics of a new model of sustained atrial fibrillation," Circulation 91:1588-1595 (1995)

Higgins C B, "Parasympathetic control of the heart," Pharmacol. Rev. 25:120-155 (1973)

Billette J et al., "Roles of the AV junction in determining the ventricular response to atrial fibrillation," Can J Physiol Pharamacol 53(4)575-85 (1975)

Garrigue S et al., "Post-ganglionic vagal stimulation of the atrioventricular node reduces ventricular rate during atrial fibrillation," PACE 21(4), 878 (Part II) (1998)

Kwan H et al., "Cardiovascular adverse drug reactions during initiation of antiarrhythmic therapy for atrial fibrillation," Can J Hosp Pharm 54:10-14 (2001)

A number of patents describe techniques for treating arrhythmias and/or ischemia by, at least in part, stimulating the vagus nerve. Arrhythmias in which the heart rate is too fast include fibrillation, flutter and tachycardia. Arrhythmia in which the heart rate is too slow is known as bradyarrhythmia.

U.S. Pat. No. 5,700,282 to Zabara, which is incorporated herein by reference, describes techniques for stabilizing the heart rhythm of a patient by detecting arrhythmias and then electronically stimulating the vagus and cardiac sympathetic nerves of the patient. The stimulation of vagus efferents directly causes the heart rate to slow down, while the stimulation of cardiac sympathetic nerve efferents causes the heart rate to quicken.

The following patents, patent application publications, and statutory invention registration, all of which are incorporated herein by reference, may be of interest:

U.S. Pat. No. 5,330,507 to Schwartz
U.S. Pat. Nos. 5,690,681 and 5,916,239 to Geddes et al.
US Patent Publication 2003/0045909 to Gross et al.
U.S. Pat. No. 6,511,500 to Rahme
U.S. Pat. Nos. 5,334,221 to Bardy and 5,356,425 to Bardy et al.
U.S. Pat. No. 5,522,854 to Ideker et al.
U.S. Pat. No. 6,434,424 to Igel et al.
US Patent Application Publication 2002/0120304 to Mest
U.S. Pat. No. 6,564,096 to Mest
U.S. Pat. No. 5,658,318 to Stroetmann et al.
U.S. Pat. No. 6,292,695 to Webster, Jr. et al.
U.S. Pat. RE38,705 to Hill et al.
US Statutory Invention Registration H1,905 to Hill,
U.S. Pat. No. 5,243,980 to Mehra
U.S. Pat. No. 5,170,802 to Mehra
U.S. Pat. No. 5,224,491 to Mehra
U.S. Pat. No. 4,161,952 to Kinney et al.
U.S. Pat. No. 6,134,470 to Hartlaub
U.S. Pat. Nos. 6,073,048 and 6,985,774 to Kieval et al.
U.S. Pat. No. 6,865,416 to Dev et al.
U.S. Pat. No. 6,161,029 to Spreigl et al.
U.S. Pat. No. 5,645,570 to Corbucci
U.S. Pat. No. 7,082,336 to Ransbury et al.

A number of patents and articles describe other methods and devices for stimulating nerves to achieve a desired effect. Often these techniques include a design for an electrode or electrode cuff. The following patents and patent application publications, all of which are incorporated herein by reference, may be of interest:

US Patent Publication 2003/0050677 to Gross et al.
U.S. Pat. No. 4,608,985 to Crish et al.
U.S. Pat. No. 4,649,936 to Ungar et al.
PCT Patent Publication WO 01/10375 to Felsen et al.
U.S. Pat. No. 5,755,750 to Petruska et al.

The following articles, which are incorporated herein by reference, may be of interest:

Ungar I J et al., "Generation of unidirectionally propagating action potentials using a monopolar electrode cuff," Annals of Biomedical Engineering, 14:437-450 (1986)

Sweeney J D et al., "An asymmetric two electrode cuff for generation of unidirectionally propagated action potentials," IEEE Transactions on Biomedical Engineering, vol. BME-33(6) (1986)

Sweeney J D et al., "A nerve cuff technique for selective excitation of peripheral nerve trunk regions," IEEE Transactions on Biomedical Engineering, 37(7) (1990)

Naples G G et al., "A spiral nerve cuff electrode for peripheral nerve stimulation," by IEEE Transactions on Biomedical Engineering, 35(11) (1988)

van den Honert C et al., "Generation of unidirectionally propagated action potentials in a peripheral nerve by brief stimuli," Science, 206:1311-1312 (1979)

van den Honert C et al., "A technique for collision block of peripheral nerve: Single stimulus analysis," MP-11, IEEE Trans. Biomed. Eng. 28:373-378 (1981)

van den Honert C et al., "A technique for collision block of peripheral nerve: Frequency dependence," MP-12, IEEE Trans. Biomed. Eng. 28:379-382 (1981)

Rijkhoff N J et al., "Acute animal studies on the use of anodal block to reduce urethral resistance in sacral root stimulation," IEEE Transactions on Rehabilitation Engineering, 2(2):92 (1994)

Mushahwar V K et al., "Muscle recruitment through electrical stimulation of the lumbo-sacral spinal cord," IEEE Trans Rehabil Eng, 8(1):22-9 (2000)

Deurloo K E et al., "Transverse tripolar stimulation of peripheral nerve: a modelling study of spatial selectivity," Med Biol Eng Comput, 36(1):66-74 (1998)

Tarver W B et al., "Clinical experience with a helical bipolar stimulating lead," Pace, Vol. 15, October, Part 11 (1992)

Manfredi M, "Differential block of conduction of larger fibers in peripheral nerve by direct current," Arch. Ital. Biol., 108:52-71 (1970)

Fitzpatrick et al., "A nerve cuff design for the selective activation and blocking of myelinated nerve fibers," Ann. Conf. of the IEEE Eng. in Medicine and Biology Soc, 13(2), 906 (1991)

Rijkhoff N J et al., "Orderly recruitment of motoneurons in an acute rabbit model," Ann. Conf. of the IEEE Eng., Medicine and Biology Soc., 20(5):2564 (1998)

Rijkhoff N J et al., "Selective stimulation of small diameter nerve fibers in a mixed bundle," Proceedings of the Annual Project Meeting Sensations/Neuros and Mid-Term Review Meeting on the TMR-Network Neuros, Apr. 21-23, 1999, pp. 20-21 (1999)

Baratta R et al., "Orderly stimulation of skeletal muscle motor units with tripolar nerve cuff electrode," IEEE Transactions on Biomedical Engineering, 36(8):836-43 (1989)

Grill W M et al., "Inversion of the current-distance relationship by transient depolarization," IEEE Trans Biomed Eng, 44(1):1-9 (1997)

Goodall EV et al., "Position-selective activation of peripheral nerve fibers with a cuff electrode," IEEE Trans Biomed Eng, 43(8):851-6 (1996)

Veraart C et al., "Selective control of muscle activation with a multipolar nerve cuff electrode," IEEE Trans Biomed Eng, 40(7):640-53 (1993)

Rattay, "Analysis of models for extracellular fiber stimulation," IEEE Transactions on Biomedical Engineering, Vol. 36, no. 2, p. 676, 1989

SUMMARY OF THE INVENTION

In some embodiments of the present invention, a system for treating a patient suffering from non-sinus atrial tachycardia comprises a control unit and an electrode device, which is configured to be applied to a site containing parasympathetic nervous tissue. Upon detection of an episode of the non-sinus atrial tachycardia, the control unit drives the electrode device to apply a signal to the nervous tissue, and configures the signal to terminate the episode, i.e., to induce cardioversion. Such non-sinus atrial tachycardia typically includes atrial fibrillation (AF) or atrial flutter. For some applications, the control unit is configured to detect the episode responsively to a physiological signal received by the control unit, while for other applications, the patient or a device external to the control unit detects the episode and activates the control unit to terminate the episode.

In some embodiments of the present invention, the electrode device is applied to a parasympathetic site of an atrium, such as an area around the pulmonary veins in the left atrium, a site in a vicinity of an insertion of a superior vena cava vein into the right atrium, a sinoatrial (SA) node fat pad, a pulmonary vein fat pad, a site in the left atrium in the vicinity of an insertion of a pulmonary vein, a site along an atrioventricular groove (e.g., a site along the coronary sinus), and a site along an intraatrial groove. For some applications, the site is on an exterior surface of the atrium, while for other applications, the site is on an internal endocardial surface of the atrium.

In some embodiments of the present invention, upon detection of an episode of non-sinus atrial tachycardia, the control unit delays application of the cardioversion signal to allow for spontaneous resolution of the episode. The control unit applies the signal if the episode does not resolve during the delay. Typically, the delay is at least about 10 seconds. The delay allows for the spontaneous return to NSR, thereby avoiding applying unnecessary stimulation. In addition, it is believed by the inventors that the transition to arrhythmia is accompanied by a strong neurohormonal response that sometimes counteracts the effect of stimulation. The delay thus provides time for this neurohormonal response to subside, after which the cardioversion signal is more likely to be effective in inducing a return to normal sinus rhythm.

In some embodiments of the present invention, the system is configured to apply a signal to stimulate atrial cardiac muscle tissue of the patient. Such stimulation in combination with application of the parasympathetic cardioversion signal helps terminate the episode of non-sinus atrial tachycardia. For some applications, the control unit configures the cardiac muscle signal to pace the atrium. For other applications, the control unit configures the cardiac muscle signal to have a greater strength than conventional atrial pacing pulses. For some applications, the cardiac muscle stimulation is delivered with the same electrode device as the parasympathetic stimulation, while for other applications, the system comprises separate electrode devices for cardiac muscle stimulation and parasympathetic stimulation. In some embodiments of the present invention, the control unit is configured to apply atrial pacing when the patient is not experiencing an episode of non-sinus atrial tachycardia, and the parasympathetic cardioversion signal during such an episode.

In an experiment conducted by the inventors, an electrode device was implanted around a right cervical vagus nerve of a dog suffering from artificially-induced severe heart failure and AF. During five separate episodes of AF, a control unit drove the electrode device to apply vagal stimulation. Cardioversion of all of the episodes was achieved within three seconds from the commencement of vagal stimulation.

In some embodiments of the present invention, a system for treating non-sinus atrial tachycardia comprises blood pressure-reducing functionality and a control unit coupled thereto. Upon the detection of episode of non-sinus atrial tachycardia, the control unit drives the functionality to cause a reduction in blood pressure of the patient sufficient to induce atrial cardioversion. Techniques for reducing blood pressure include electrical stimulation of a parasympathetic site, electrical stimulation of one or more baroreceptors, reduction of the forward activity of a ventricular assist device, activation of a control valve implanted at a venous site for obstruction of blood flow, and administration of a blood pressure-lowering drug.

There is therefore provided, in accordance with an embodiment of the present invention, apparatus including:

an electrode device, configured to be coupled to an atrial site of a subject containing parasympathetic nervous tissue; and a control unit, configured to, responsively to a detection of an episode of non-sinus atrial tachycardia, restore normal sinus rhythm (NSR) of the subject, by:

driving the electrode device to apply a parasympathetic stimulation signal to the atrial site, and configuring the parasympathetic stimulation signal to activate the parasympathetic nervous tissue sufficiently to restore the NSR.

In an embodiment of the present invention, the non-sinus atrial tachycardia includes atrial fibrillation (AF), and the control unit is configured to restore the NSR responsively to the detection of the episode of the AF. Alternatively, the non-sinus atrial tachycardia includes atrial flutter, and the control unit is configured to restore the NSR responsively to the detection of the episode of the atrial flutter.

For some applications, the electrode device includes an intravascular electrode lead. Alternatively, the electrode device is configured to be placed at an epicardial site.

For some applications, the atrial site is selected from the group consisting of: an area around pulmonary veins in a left atrium, a site in a vicinity of an insertion of a superior vena cava vein into a right atrium, an atrial fat pad, a sinoatrial (SA) node fat pad, a pulmonary vein fat pad, and a site in the left atrium in the vicinity of an insertion of a pulmonary vein, and the electrode device is configured to be coupled to the selected atrial site. Alternatively, the atrial site is selected from the group consisting of: a site along an atrioventricular groove, a site along a coronary sinus, and a site along an intraatrial groove, and the electrode device is configured to be coupled to the selected atrial site.

For some applications, the control unit is configured to apply the parasympathetic stimulation signal at between 50 and 200 pulses per second. For some applications, the control unit is configured to configure the parasympathetic stimulation signal to include at least one monophasic pulse, and the control unit is configured to withhold discharging the atrial site for at least 5 ms after completing application of the at least one monophasic pulse.

For some applications, the control unit is configured to restore the NSR by: driving the electrode device to apply the parasympathetic stimulation signal and configuring the parasympathetic stimulation signal to activate the parasympathetic nervous tissue at a first strength during a first stimulation session, and responsively to a determination that the episode has not been resolved, driving the electrode device to apply the parasympathetic stimulation signal and configuring the parasympathetic stimulation signal to activate the parasympathetic nervous tissue at a second strength during a second stimulation session subsequent to the first stimulation session, wherein the second strength is greater than the first strength.

For some applications, the apparatus includes an external unit, which includes circuitry, configured to perform the detection of the episode; and a wireless transmitter, configured to send a wireless signal to the control unit responsively to the detection. For some applications, the wireless signal includes one or more parameters of the parasympathetic stimulation signal. Alternatively or additionally, the wireless signal includes power sufficient to power the electrode device.

In an embodiment, the electrode device is configured to sense electrical activity at the atrial site, and the detection is performed at least partially responsively to the sensed electrical activity. For some applications, the electrode device includes first and second electrodes, and the electrode device is configured to sense the electrical activity using at least the first electrode, and the control unit is configured to restore the NSR by driving at least the first electrode to apply the parasympathetic stimulation signal to the atrial site.

In an embodiment, the control unit is configured to be placed within a blood vessel of the subject. For some applications, the blood vessel includes a vena cava of the subject, and the control unit is configured to be placed within the vena cava.

In an embodiment, the control unit is configured to apply a cardiac muscle signal to at least one atrium of the subject selected from the group consisting of: an atrium including the atrial site, and an atrium contralateral to the atrium including the atrial site, and to configure the cardiac muscle signal to stimulate cardiac muscle tissue. For some applications, the at least one atrium includes the atrium including the atrial site, and the control unit is configured to drive the electrode device to apply the cardiac muscle signal to the atrial site.

In an embodiment, the electrode device includes a first electrode device, the atrial site includes a first atrial site, the apparatus includes a second electrode device, configured to be coupled to a second atrial site of the at least one atrium, and the control unit is configured to drive the second electrode device to apply the cardiac muscle signal to the second atrial site.

In an embodiment, the control unit is configured to apply the cardiac muscle signal responsively to the detection, and to configure the cardiac muscle signal to restore the NSR.

In an embodiment, the control unit is configured to set a strength of the cardiac muscle signal to be greater than that necessary for pacing the at least one atrium. For some applications, the control unit is configured to set a pulse duration of the cardiac muscle signal to be at least 0.5 ms.

In an embodiment, the control unit is configured to configure the cardiac muscle signal to pace the at least one atrium. For some applications, the control unit is configured to apply the cardiac muscle signal during at least a portion of the time when the subject is not experiencing the episode.

In an embodiment, the control unit is configured to configure the cardiac muscle signal to pace the at least one atrium during at least a portion of the time when the subject is not experiencing the episode, and responsively to the detection, configure the cardiac muscle signal to restore the NSR. For some applications, the control unit is configured to configure the cardiac muscle signal to restore the NSR by setting a strength of the cardiac muscle signal to be greater than that necessary for pacing the at least one atrium. For example, the control unit may be configured to set a pulse duration of the cardiac muscle signal to be at least 0.5 ms.

In an embodiment, the control unit is configured to drive the electrode device to apply the parasympathetic stimulation signal during a first period, and the cardiac muscle signal during a second period different from the first period. For some applications, the first period includes a ventricular total refractory period, and the control unit is configured to drive the electrode device to apply the parasympathetic stimulation signal during the ventricular total refractory period. Alternatively or additionally, the second period includes a ventricular relative refractory period, and the control unit is configured to drive the electrode device to apply the cardiac muscle signal during the ventricular relative refractory period.

In an embodiment, the control unit is configured to synchronize the parasympathetic stimulation signal with a feature of a cardiac cycle of the subject. For some applications, the control unit is configured to apply the parasympathetic stimulation signal during a ventricular refractory period of the cardiac cycle.

In an embodiment, the control unit is configured to begin to apply the parasympathetic stimulation signal after a delay after the detection, if the episode has not been resolved during the delay. For some applications, the delay has a duration of at least 5 seconds, e.g., at least 10 seconds.

In an embodiment, the control unit is configured to apply the parasympathetic stimulation signal at a first strength during a first period, and at a second strength greater than the first strength during a second period after the first period. For some applications, the first and second periods each have a duration of at least two seconds, and the control unit is configured to provide a delay between a conclusion of the first period and a commencement of the second period having a duration of at least five seconds.

There is further provided, in accordance with an embodiment of the present invention, apparatus including:
an electrode device, configured to be coupled to a site of a subject containing parasympathetic nervous tissue; and
a control unit, configured to:
responsively to a detection of an episode of non-sinus atrial tachycardia, wait during a delay period, and
upon conclusion of the delay period, responsively to a determination that the episode has not been resolved, restore normal sinus rhythm (NSR) of the subject by:
driving the electrode device to apply a parasympathetic stimulation signal to the site, and
configuring the parasympathetic stimulation signal to activate the parasympathetic nervous tissue sufficiently to restore the NSR.

For some applications, the delay period has a duration of at least ten seconds.

For some applications, the non-sinus atrial tachycardia includes atrial fibrillation (AF), and the control unit is configured to restore the NSR responsively to the detection of the episode of the AF. Alternatively, the non-sinus atrial tachycardia includes atrial flutter, and the control unit is configured to restore the NSR responsively to the detection of the episode of the atrial flutter.

For some applications, the apparatus includes a sensor configured to sense a physiological parameter of the subject, and generate a sensor signal responsively thereto, and the control unit is configured to receive the sensor signal, and, responsively thereto, perform the detection of the episode and make the determination that the episode has not been resolved.

For some applications, the control unit is configured to receive one or more communication signals indicative of the detection of the episode and of the determination that the episode has not resolved.

For some applications, the site is selected from the group consisting of: a vagus nerve, an epicardial fat pad, a sinoatrial (SA) node fat pad, a pulmonary vein, a carotid artery, a carotid sinus, a coronary sinus, a vena cava vein, a jugular vein, an azygos vein, an innominate vein, a subclavian vein, a right ventricle, a right atrium, an area around pulmonary veins in a left atrium, a site in a vicinity of an insertion of a superior vena cava vein into a right atrium, an atrial fat pad, a pulmonary vein fat pad, and a site in the left atrium in the vicinity of an insertion of a pulmonary vein, and the electrode device is configured to be applied to the selected site. Alternatively, the site is selected from the group consisting of: a site along an atrioventricular groove, a site along a coronary sinus, and a site along an intraatrial groove, and the electrode device is configured to be coupled to the selected site.

There is still further provided, in accordance with an embodiment of the present invention, apparatus including:

an electrode device, configured to be coupled to a site of a subject containing parasympathetic nervous tissue, and to sense electrical activity at the site; and a control unit, configured to, responsively to a detection of an episode of non-sinus atrial tachycardia, which detection is performed at least partially responsively to the sensed electrical activity, restore normal sinus rhythm (NSR) of the subject by:

driving the electrode device to apply a parasympathetic stimulation signal to the site, and configuring the parasympathetic stimulation signal to activate the parasympathetic nervous tissue sufficiently to restore the NSR.

In an embodiment of the present invention, the electrode device includes first and second electrodes, and the electrode device is configured to sense the electrical activity using at least the first electrode, and the control unit is configured to restore the NSR by driving at least the first electrode to apply the parasympathetic stimulation signal to the site.

For some applications, the site is selected from the group consisting of: an epicardial fat pad, a sinoatrial (SA) node fat pad, a pulmonary vein, a carotid artery, a carotid sinus, a coronary sinus, a vena cava vein, a jugular vein, an azygos vein, an innominate vein, a subclavian vein, a right ventricle, a right atrium, an area around pulmonary veins in a left atrium, a site in a vicinity of an insertion of a superior vena cava vein into a right atrium, an atrial fat pad, a pulmonary vein fat pad, and a site in the left atrium in the vicinity of an insertion of a pulmonary vein, and the electrode device is configured to be applied to the selected site. Alternatively, the site is selected from the group consisting of: a site along an atrioventricular groove, a site along a coronary sinus, and a site along an intraatrial groove, and the electrode device is configured to be coupled to the selected site.

For some applications, the non-sinus atrial tachycardia includes atrial fibrillation (AF), and the control unit is configured to restore the NSR responsively to the detection of the episode of the AF. Alternatively, the non-sinus atrial tachycardia includes atrial flutter, and the control unit is configured to restore the NSR responsively to the detection of the episode of the atrial flutter.

There is additionally provided, in accordance with an embodiment of the present invention, apparatus including:

a first electrode device, configured to be coupled to a parasympathetic site of a subject containing parasympathetic nervous tissue;

a second electrode device, configured to be coupled to an atrial site of an atrium of the subject; and a control unit, configured to:

drive the second electrode device to apply a cardiac muscle signal to the atrial site, and configure the cardiac muscle signal to stimulate cardiac muscle tissue, and responsively to a detection of an episode of non-sinus atrial tachycardia, restore normal sinus rhythm (NSR) of the subject by:

driving the first electrode device to apply a parasympathetic stimulation signal to the parasympathetic site, and configuring the parasympathetic stimulation signal to activate the parasympathetic nervous tissue sufficiently to restore the NSR.

For some applications, the parasympathetic site is selected from the group consisting of: a vagus nerve, an epicardial fat pad, a sinoatrial (SA) node fat pad, a pulmonary vein, a carotid artery, a carotid sinus, a coronary sinus, a vena cava vein, a jugular vein, an azygos vein, an innominate vein, a subclavian vein, a right ventricle, a right atrium, an area around pulmonary veins in a left atrium, a site in a vicinity of an insertion of a superior vena cava vein into a right atrium, an atrial fat pad, a pulmonary vein fat pad, and a site in the left atrium in the vicinity of an insertion of a pulmonary vein, and the first electrode device is configured to be applied to the selected parasympathetic site. Alternatively, the parasympathetic site is selected from the group consisting of: a site along an atrioventricular groove, a site along a coronary sinus, and a site along an intraatrial groove, and the first electrode device is configured to be coupled to the selected parasympathetic site.

For some applications, the non-sinus atrial tachycardia includes atrial fibrillation (AF), and the control unit is configured to restore the NSR responsively to the detection of the episode of the AF. Alternatively, the non-sinus atrial tachycardia includes atrial flutter, and the control unit is configured to restore the NSR responsively to the detection of the episode of the atrial flutter.

In an embodiment of the present invention, the control unit is configured to apply the cardiac muscle signal responsively to the detection, and to configure the cardiac muscle signal to restore the NSR.

In an embodiment, the control unit is configured to set a strength of the cardiac muscle signal to be greater than that necessary for pacing the atrium. For some applications, the control unit is configured to configure the cardiac muscle signal to have a pulse duration greater than that necessary for pacing the atrium. For example, the control unit may be configured to set the pulse duration to be at least 0.5 ms, such as at least 2 ms.

In an embodiment, the control unit is configured to configure the cardiac muscle signal to pace the atrium. For some applications, the control unit is configured to apply the cardiac muscle signal during at least a portion of the time when the subject is not experiencing the episode.

In an embodiment, the control unit is configured to configure the cardiac muscle signal to pace the atrium during at least a portion of the time when the subject is not experiencing the episode, and responsively to the detection, configure the cardiac muscle signal to restore the NSR. For some applications, the control unit is configured to configure the cardiac muscle signal to restore the NSR by setting a strength of the cardiac muscle signal to be greater than that necessary for pacing the atrium. For some applications, the control unit is configured to configure the cardiac muscle signal to restore the NSR by setting a pulse duration of the cardiac muscle signal to be greater than that necessary for pacing the atrium. For example, the control unit may be configured to set the pulse duration to be at least 0.5 ms, such as at least 2 ms.

There is yet additionally provided, in accordance with an embodiment of the present invention, apparatus for treating a subject, including:

blood pressure-lowering functionality; and a control unit, configured to, responsively to a detection of an episode of non-sinus atrial tachycardia, restore normal sinus rhythm (NSR) of the subject by driving the blood pressure-lowering functionality to lower a blood pressure of the subject sufficiently to restore the NSR.

For some applications, the apparatus includes a blood pressure sensor configured to generate a blood pressure signal, and the control unit is configured to lower the blood pressure to a target level responsively to the blood pressure signal.

In an embodiment, the blood pressure-lowering functionality includes an electrode device, configured to be coupled to a site of the subject containing parasympathetic nervous tissue, and the control unit is configured to drive the electrode device to apply a parasympathetic stimulation signal to the site, responsively to the detection, and to configure the parasympathetic stimulation signal to stimulate the parasympathetic nervous tissue to lower the blood pressure sufficiently to restore the NSR.

In an embodiment, the blood pressure-lowering functionality includes an electrode device, configured to be coupled to a site of the subject in vicinity of a baroreceptor, and the control unit is configured to drive the electrode device to apply an electrical signal to the site, responsively to the detection, and to configure the signal to lower the blood pressure sufficiently to restore the NSR. For some applications, the site is selected from the group consisting of: a carotid bifurcation, and a jugular vein, and the electrode device is configured to be coupled to the selected site.

In an embodiment, the blood pressure-lowering functionality includes a ventricular assist device, and the control unit is configured to drive the ventricular assist device to reduce forward activity thereof to lower the blood pressure sufficiently to restore the NSR.

In an embodiment, the blood pressure-lowering functionality includes a control valve, configured to be implanted at a venous site for obstruction of blood flow, and the control unit is configured to drive the control valve to lower the blood pressure sufficiently to restore the NSR.

In an embodiment, the blood pressure-lowering functionality includes a drug administration device containing a blood pressure-lowering drug, and the control unit is configured to drive the drug administration device to administer the drug in a dosage sufficient to lower the blood pressure sufficiently to restore the NSR.

For some applications, the non-sinus atrial tachycardia includes atrial fibrillation (AF), and the control unit is configured to restore the NSR responsively to the detection of the episode of the AF. Alternatively, the non-sinus atrial tachycardia includes atrial flutter, and the control unit is configured to restore the NSR responsively to the detection of the episode of the atrial flutter.

There is also provided, in accordance with an embodiment of the present invention, apparatus including:

an electrode device, configured to be coupled to a site of a subject containing parasympathetic nervous tissue; and circuitry, configured to:

be placed in a blood vessel of the subject, and responsively to a detection of an episode of non-sinus atrial tachycardia, restore normal sinus rhythm (NSR) of the subject, by:

driving the electrode device to apply a parasympathetic stimulation signal to the site, and configuring the parasympathetic stimulation signal to activate the parasympathetic nervous tissue sufficiently to restore the NSR.

In an embodiment, the blood vessel includes a vena cava of the subject, and the circuitry is configured to be placed within the vena cava.

For some applications, the apparatus includes a housing, which includes the circuitry and the electrode device, and the housing is configured to be placed in the blood vessel.

There is further provided, in accordance with an embodiment of the present invention, apparatus including:

a non-implantable transmitter, configured to transmit a wireless signal responsively to a detection of an episode of non-sinus atrial tachycardia;

an implantable electrode device, configured to be coupled to a site of a subject containing parasympathetic nervous tissue; and circuitry, configured to:

be placed in a blood vessel of the subject, receive the wireless signal, and responsively to the wireless signal, restore normal sinus rhythm (NSR) of the subject, by driving the electrode device to apply, to the site, a parasympathetic stimulation signal configured to activate the parasympathetic nervous tissue sufficiently to restore the NSR.

In an embodiment, the blood vessel includes a vena cava of the subject, and the circuitry is configured to be placed within the vena cava.

In an embodiment, the apparatus includes a physiological sensor, configured to sense a physiological parameter of the subject; and a non-implantable monitor, configured to perform the detection of the episode responsively to the sensed physiological parameter.

For some applications, the wireless signal includes one or more parameters of the parasympathetic stimulation signal. Alternatively or additionally, the wireless signal includes power sufficient to power the electrode device.

For some applications, the apparatus includes a housing, which includes the circuitry and the electrode device, and the housing is configured to be placed in the blood vessel.

There is still further provided, in accordance with an embodiment of the present invention, apparatus including:

a tracheal electrode device, configured to be placed in a trachea of a subject in a vicinity of at least one thoracic vagus nerve of the subject; and circuitry, configured to:

drive the electrode device to apply an electrical current to a wall of the trachea, and configure the current to stimulate the at least one thoracic vagus nerve.

For some applications, the circuitry is configured to configure the current to activate the at least one thoracic vagus nerve. Alternatively, the circuitry is configured to configure the current to inhibit the at least one thoracic vagus nerve.

There is additionally provided, in accordance with an embodiment of the present invention, apparatus including:

an esophageal electrode device, configured to be placed in an esophagus of a subject in a vicinity of at least one vagus nerve of the subject; and circuitry, configured to:

drive the electrode device to apply an electrical current to a wall of the esophagus, and configure the current to stimulate the at least one vagus nerve.

There is yet additionally provided, in accordance with an embodiment of the present invention, a method including:

detecting an episode of non-sinus atrial tachycardia of a subject; and responsively to the detecting, restoring normal sinus rhythm (NSR) of the subject, by:

applying a parasympathetic stimulation signal to an atrial site of the subject containing parasympathetic nervous tissue, and configuring the parasympathetic stimulation signal to activate the parasympathetic nervous tissue sufficiently to restore the NSR.

In an embodiment, configuring the parasympathetic stimulation signal includes setting, during a calibration procedure, at least one parameter of the parasympathetic stimulation signal to have a minimum value sufficient to achieve a desired effect. For some applications, the desired effect includes a decrease in an atrial effective refractory period (AERP) of the subject, a reduction in systolic blood pressure of the subject, a reduction in a heart rate of the subject, and/or prolongation of a P-R interval of the subject.

In an embodiment, configuring the parasympathetic stimulation signal includes determining, during a calibration procedure, a maximum value of at least one parameter of the parasympathetic stimulation signal that is safe for the subject. For some applications, determining the maximum value includes determining the maximum value that does not reduce systolic blood pressure below a threshold value, determining the maximum value that does not cause complete AV block, and/or determining the maximum value that does not result in ventricular capture.

In an embodiment, the method includes performing, prior to detecting the episode, an acute test to determine whether the subject is expected to benefit from the applying the parasympathetic stimulation signal. For some applications, performing the acute test includes stimulating the atrial site.

There is also provided, in accordance with an embodiment of the present invention, a method including:

detecting of an episode of non-sinus atrial tachycardia of a subject;

responsively to the detecting, waiting during a delay period; and upon conclusion of the delay period, responsively to a determination that the episode has not been resolved, restoring normal sinus rhythm (NSR) of the subject by:

applying a parasympathetic stimulation signal to a site of a subject containing parasympathetic nervous tissue, and configuring the parasympathetic stimulation signal to activate the parasympathetic nervous tissue sufficiently to restore the NSR.

There is further provided, in accordance with an embodiment of the present invention, a method including:

coupling an electrode device to a site of a subject containing parasympathetic nervous tissue;

sensing electrical activity at the site using the electrode device;

detecting an episode of non-sinus atrial tachycardia, at least partially responsively to the sensed electrical activity; and responsively to the detecting, restoring normal sinus rhythm (NSR) of the subject by:

apply a parasympathetic stimulation signal to the site using the electrode device, and configuring the parasympathetic stimulation signal to activate the parasympathetic nervous tissue sufficiently to restore the NSR.

There is still further provided, in accordance with an embodiment of the present invention, a method including:

applying a cardiac muscle signal to an atrial site of an atrium of a subject;

configuring the cardiac muscle signal to stimulate cardiac muscle tissue;

detecting an episode of non-sinus atrial tachycardia of the subject; and responsively to the detecting, restoring normal sinus rhythm (NSR) of the subject, by:

applying a parasympathetic stimulation signal to a parasympathetic site of the subject containing parasympathetic nervous tissue, and configuring the parasympathetic stimulation signal to activate the parasympathetic nervous tissue sufficiently to restore the NSR.

There is additionally provided, in accordance with an embodiment of the present invention, a method for treating a subject, including:

detecting an episode of non-sinus atrial tachycardia of the subject; and responsively to the detecting, restoring normal sinus rhythm (NSR) of the subject by lowering a blood pressure of the subject sufficiently to restore the NSR.

There is yet additionally provided, in accordance with an embodiment of the present invention, a method including:

placing circuitry in a blood vessel of a subject;

detecting an episode of non-sinus atrial tachycardia of the subject; and responsively to the detecting, restoring normal sinus rhythm (NSR) of the subject, by:

driving, by the circuitry, application of a parasympathetic stimulation signal to a site of the subject containing parasympathetic nervous tissue, and configuring the parasympathetic stimulation signal to activate the parasympathetic nervous tissue sufficiently to restore the NSR.

There is also provided, in accordance with an embodiment of the present invention, a method including:

placing circuitry in a blood vessel of a subject;

detecting an episode of non-sinus atrial tachycardia of the subject;

transmitting, from outside a body of the subject, a wireless signal responsively to the detecting;

receiving the wireless signal by the circuitry; and responsively to the wireless signal, restoring normal sinus rhythm (NSR) of the subject, by:

driving, by the circuitry, application of a parasympathetic stimulation signal to a site of the subject containing parasympathetic nervous tissue, and configuring the parasympathetic stimulation signal to activate the parasympathetic nervous tissue sufficiently to restore the NSR.

There is further provided, in accordance with an embodiment of the present invention, a method including:

applying, from within a trachea of a subject, an electrical current to a wall of the trachea in a vicinity of at least one thoracic vagus nerve of the subject; and configuring the current to stimulate the at least one thoracic vagus nerve.

There is still further provided, in accordance with an embodiment of the present invention, a method including:

applying, from within an esophagus of a subject, an electrical current to a wall of the esophagus in a vicinity of at least one vagus nerve of the subject; and configuring the current to stimulate the at least one vagus nerve.

The present invention will be more fully understood from the following detailed description of embodiments thereof, taken together with the drawings, in which:

BRIEF DESCRIPTION OF THE DRAWINGS

FIG. 4 is a flow chart that schematically illustrates a method for determining and applying an appropriate atrial fibrillation treatment based on a countdown, in accordance with an embodiment of the present invention;

FIGS. 6A-B are schematic perspective and cross-sectional illustrations, respectively, of a tracheal stimulation system, in accordance with an embodiment of the present invention.

DETAILED DESCRIPTION OF EMBODIMENTS

Figure 1:
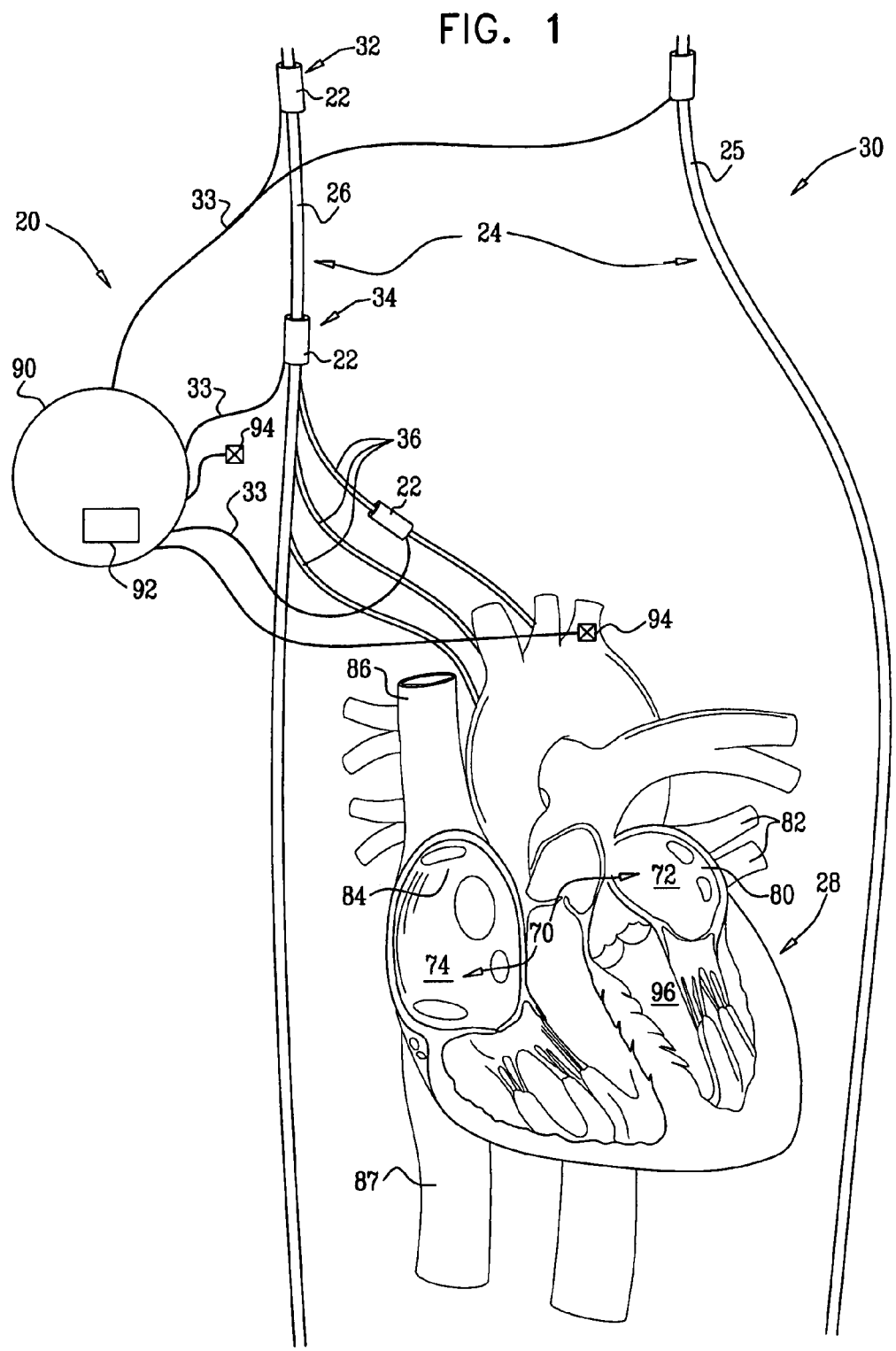
FIG. 1 is a schematic illustration of a system for treating a patient suffering from non-sinus atrial tachycardia, in accordance with an embodiment of the present invention.

FIG. 1 is a schematic illustration of a system 20 for treating a patient 30 suffering from non-sinus atrial tachycardia, in accordance with an embodiment of the present invention. Typically, the non-sinus atrial tachycardia includes atrial fibrillation (AF) or atrial flutter. System 20 comprises at least one electrode device 22, which is applied to a site of patient 30 containing parasympathetic nervous tissue.

In an embodiment of the present invention, electrode device 22 is applied to a vagus nerve 24 (either a left vagus nerve 25 or a right vagus nerve 26), which innervates a heart 28 of patient 30. For some applications, electrode device 22 is applied to: (a) a cervical site 32 of the vagus nerve; (b) a thoracic site 34 of the vagus nerve, above one or more of the junctions at which cardiac branches 36 of the vagus nerve branch off from the vagus nerve; or (c) a branch of the vagus nerve, such as one of the cardiac branches 36 (e.g., the superior cardiac nerve, the superior cardiac branch, and the inferior cardiac branch).

In an embodiment of the present invention, electrode device 22 is applied to a site of patient 30 selected from the group consisting of: a vena cava vein (either a superior vena cava 86 or an inferior vena cava 87), a jugular vein (e.g., an internal jugular vein), a pulmonary vein 82, a carotid artery, a carotid sinus, a coronary sinus, an epicardial fat pad, a sinoatrial (SA) node fat pad, a pulmonary vein fat pad, an azygos vein, an innominate vein, a subclavian vein, a right ventricle, a right atrium, an area around the pulmonary veins in the left atrium, a site in a vicinity of an insertion of a superior vena cava vein into the right atrium, a site in the left atrium in the vicinity of an insertion of a pulmonary vein, a site along an atrioventricular groove (e.g., a site along the coronary sinus), and a site along an intraatrial groove.

In an embodiment of the present invention, electrode device 22 is applied to a parasympathetic site of an atrium 70 (a left atrium 72 or a right atrium 74). As used in the present application, including in the claims, an "atrial parasympathetic site" is a site in or on the atrium, the electrical stimulation of which can induce an acute vagomimetic response. Atrial parasympathetic sites include, but are not limited to, an area 80 around pulmonary veins 82 in left atrium 72, a site 84 in a vicinity of an insertion of a superior vena cava vein 86 into right atrium 74, a sinoatrial (SA) node fat pad, a pulmonary vein fat pad, a site in the left atrium in the vicinity of an insertion of a pulmonary vein, a site along an atrioventricular groove (e.g., a site along the coronary sinus), and a site along an intraatrial groove. For some applications, electrode device 22 is configured to be positioned during an open chest surgical procedure. For example, the electrode device may be placed at an epicardial site, such as around the pulmonary veins or over fat pads. For other applications, the electrode device comprises an intravascular lead.

In an embodiment of the present invention, a procedure for applying electrode device 22 to a site in left atrium 72 comprises inserting the electrode device into right atrium 74, such as via a peripheral vein, and advancing the electrode device through a puncture of the intra-atrial septum, into left atrium 7. Once in the left atrium, electrode device 22 is either applied to a site on an internal surface of the wall of the left atrium, or is passed through the atrial wall and brought in contact with an external surface of the left atrium, and/or with a fat pad overlying the left atrium, such as a pulmonary vein fat pad.

For some applications, electrode device 22 is applied to a right atrial site by passing the electrode device through the right atrial wall and bringing the electrode device in contact with an external surface of the right atrium, and/or with a fat pad overlying the atrium, such as an SA fat pad. In an embodiment, electrode device 22 is passed through the right atrial wall and brought in contact with an external surface or fat pad of the left atrium.

In an experiment conducted by the inventors, an electrode device was implanted around a right cervical vagus nerve of a dog suffering from artificially-induced severe heart failure and AF. During five separate episodes of AF, a control unit drove the electrode device to apply vagal stimulation with an amplitude of 10 mA, at 20 bursts per second, with each burst including 4 pulses having a pulse width of 1 ms. Cardioversion of all of the episodes was achieved within three seconds from the commencement of vagal stimulation.

For some applications, in order to precisely locate the electrode assembly for stimulation of an atrial parasympathetic site, the placement procedure comprises temporarily placing the electrode assembly at one or more locations, and performing an acute test at each of the locations to determine which location shows a substantial vagomimetic effect, e.g., a reduction in heart rate. The electrode assembly is then fixated at the determined site. For some applications, this technique is used for placement of the electrode assembly at parasympathetic sites other than atrial sites, such as those parasympathetic sites mentioned hereinabove.

System 20 further comprises an implanted or external control unit 90, which typically communicates with electrode device 22 over a set of leads 33. For some applications, system 20 comprises two or more electrode devices 22. For some applications, control unit 90 is adapted to drive electrode device 22 to apply a signal to vagus nerve 24, and to configure the signal to induce the propagation of efferent nerve impulses towards heart 28.

Control unit 90 is typically adapted to receive and analyze one or more sensed physiological parameters or other parameters of patient 30, such as heart rate, electrocardiogram (ECG), blood pressure, indicators of decreased cardiac contractility, cardiac output, norepinephrine concentration, baroreflex sensitivity, or motion of the patient. In order to receive these sensed parameters, control unit 90 may comprise, for example, an ECG monitor 92, connected to a site on the patient's body such as heart 28, for example using one or more subcutaneous sensors or ventricular and/or atrial intracardiac sensors. The control unit may also comprise an accelerometer for detecting motion of the patient. Alternatively, ECG monitor 92 and/or the accelerometer comprise separate implanted devices placed external to control unit 90, and, optionally, external to the patient's body. Alternatively or additionally, control unit 90 receives signals from one or more physiological sensors 94, such as blood pressure sensors. For some applications, control unit 90 comprises or is coupled to an implantable cardioverter defibrillator (ICD) and/or a pacemaker (e.g., a bi-ventricular or standard pacemaker).

Figure 2A:
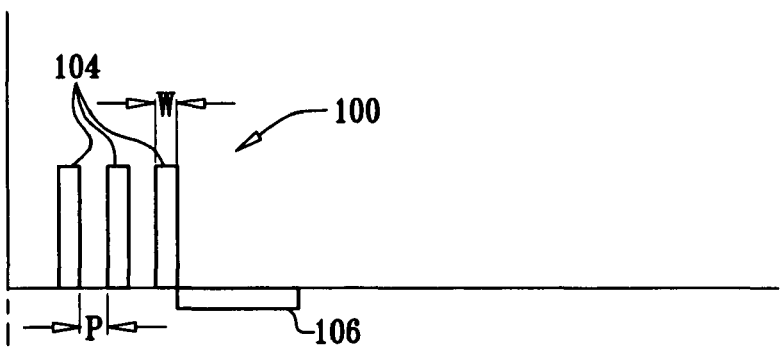
FIGS. 2A and 2B are graphs illustrating a signal applied by the system of FIG. 1 and a resulting electrical potential at a stimulation site, respectively, in accordance with an embodiment of the present invention.
Figure 2B:
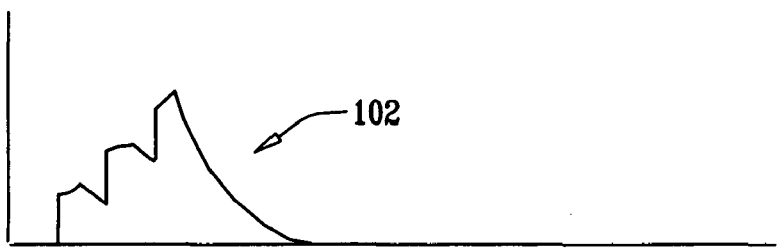

Reference is made to FIGS. 2A and 2B, which are graphs illustrating a signal 100 applied by control unit 90 and a resulting electrical potential 102 at the stimulation site, respectively, in accordance with an embodiment of the present invention. Signal 100 includes one or more monophasic pulses 104, each of which typically has a pulse width W of between about 0.1 and about 5 ms, e.g., about 1 ms. The pulses are typically separated by an interpulse period P of between about 2 and about 100 ms, e.g., about 6 ms. Substantially immediately upon completing application of the last of pulses 104, control unit 90 discharges the stimulation site by applying at least one monophasic pulse 106 of opposite charge to pulses 104. The control unit typically applies pulse 106 until the electrical potential at the stimulation site returns to approximately zero. For some applications, the control unit is configured to sense that the potential has returned to approximately zero, while for other applications, the control unit is programmed to apply a total charge estimated to result in a potential of approximately zero. Typically, an amplitude of pulse 106 is between about 2% and 20%, e.g., about 5%, of an amplitude of pulses 104, in order to prevent undesired stimulation by pulse 106.

Figure 3A:
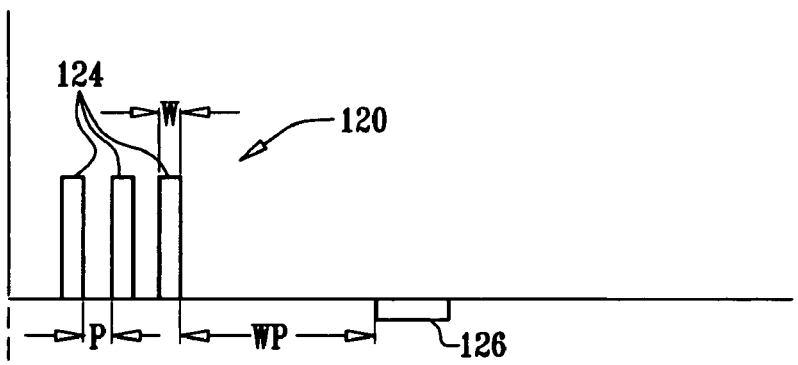
FIGS. 3A and 3B are graphs illustrating another signal applied by the system of FIG. 1 and a resulting electrical potential at the stimulation site, respectively, in accordance with an embodiment of the present invention.
Figure 3B:
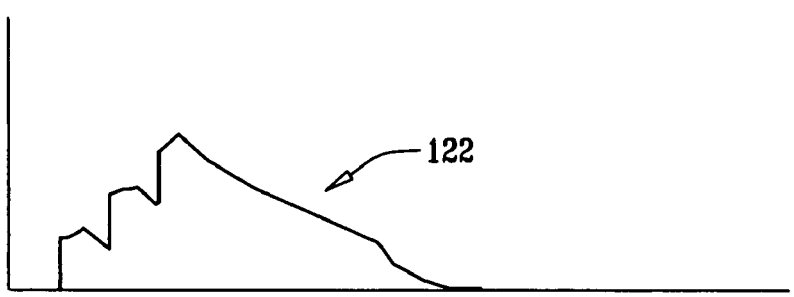

Reference is made to FIGS. 3A and 3B, which are graphs illustrating a signal 120 applied by control unit 90 and a resulting electrical potential 122 at the stimulation site, respectively, in accordance with an embodiment of the present invention. Signal 100 includes one or more monophasic pulses 104, each of which typically has a pulse width W of between about 0.1 and about 5 ms, e.g., about 1 ms. The pulses are typically separated by an interpulse period P of between about 2 and about 100 ms, e.g., about 6 ms. Upon completing application of the last of pulses 124, control unit 90 is configured to withhold discharging the stimulation site for a withholding period WP before applying at least one monophasic pulse 126 of opposite charge to pulses 124. The withholding period typically has a duration of at least 5 ms, e.g., at least 10 ms. The control unit typically applies pulse 126 until the electrical potential at the stimulation site returns to approximately zero. For some applications, the control unit is configured to sense that the potential has returned to approximately zero, while for other applications, the control unit is programmed to apply a total charge estimated to result in a potential of approximately zero. Typically, an amplitude of pulse 126 is between about 2% and 20%, e.g., about 5%, of an amplitude of pulses 124, in order to prevent undesired stimulation by pulse 126. The resulting unbalanced pulses cause either a negative or a positive local electrical potential, which locally suppresses the generation of action potentials, thereby preventing arrhythmia reentry in the area of the stimulation site. For example, this technique may be used when electrode device 22 is applied to atrial tissue.

In an embodiment of the present invention, system 20 comprises a single set of one or more electrode devices 22 that are coupled to one or more respective sites of patient 30 containing parasympathetic nervous tissue, such as one or more atrial sites. Control unit 90 uses the set to both apply parasympathetic electrical stimulation and to sense cardiac activity of the patient. For some applications, the control unit uses a single electrode device 22 for such stimulation and sensing. For some applications, the electrode device comprises at least first and second electrodes, and the control unit uses the first electrode for both stimulation and sensing. For some applications, the second electrode is placed remotely from the one or more sites, such as at a contralateral site (e.g., the first electrode may be placed in a subclavian vein, and the second electrode may be placed in the contralateral subclavian vein).

In an embodiment of the present invention, upon detection of an episode of non-sinus atrial tachycardia, control unit 90 drives electrode device 22 to apply a signal to the nervous tissue of the site to which the electrode device is applied, and configures the signal to terminate the episode, i.e., to induce cardioversion. For some applications, the control unit is configured to detect the episode responsively to one or more of the sensed physiological parameters of patient 30 described hereinabove. For example, the control unit may analyze a sensed ECG of the patient to detect the episode, as is known to those skilled in the art.

Alternatively or additionally, system 20 is activated by a signal from outside of the system, such as outside a body of patient 30. For some applications, a monitor external to the system detects an episode of the non-sinus atrial tachycardia. Alternatively or additionally, patient 30 activates the system upon feeling symptoms associates with an episode. For example, the patient or a caregiver may touch a wand to the surface of the body near the control unit. For some applications in which control unit 90 is implanted in patient 30, such activation includes the wireless transmission of power from outside of the body to the control unit, such as electromagnetically or by induction.

In an embodiment of the present invention, control unit 90 is configured to apply the cardioversion signal in one or more sessions, and to set a duration of each of the sessions to be between about 2 and about 10 seconds, e.g., between about 2 and about 5 seconds. For some applications, the signal is applied with a frequency of between about 50 and about 100 Hz and/or between about 50 and about 200 pulses per second, and/or an amplitude of between about 5 and about 30 mA, e.g., about 10 mA.

For some applications, the cardioversion signal is applied in a series of bursts, each of which includes a plurality of pulses. For example, the control unit may apply between about 5 and about 30 bursts per second, e.g., about 20 bursts per second, with each of the bursts including between about 3 and about 5 pulses, e.g., about 4 pulses (pulses per trigger, or PPT). As described hereinbelow, for some applications these parameters are calibrated for each individual patient, such as during a calibration test procedure.

For some applications, the control unit synchronizes the application of the signal with a feature of the cardiac cycle. For example, the application of the signal may commence after a delay after a detected R-wave, P-wave, or other feature of an ECG. For some applications, application of the signal commences or is applied entirely during a period of total or relative ventricular refractoriness. For example, the signal may be applied beginning at the first negative QRS deflection, and concluding within about 250 ms thereafter. Application of the signal during this period generally reduces the likelihood of undesired ventricular capture. Alternatively, for some applications, the control unit is configured to synchronize application of the signal with other physiological activity of the subject, such as respiration, muscle contractions, or spontaneous nerve activity.

Typically, upon completion of each cardioversion session, control unit 90 determines whether the episode has been successfully resolved. If the control unit finds that the episode has not been resolved, the control unit applies the cardioversion signal in a further session. The control unit typically provides a delay between completion of a session and the commencement of the following session, such as at least about 5 seconds, e.g., at least about 10 seconds, at least about one minutes, or at least about 10 minutes.

For some applications, the control unit increases the strength of the applied signal from session to session (either during each subsequent session, or a portion of the subsequent sessions), such as by increasing an amplitude of the signal, the PPT of the signal, or the frequency of the signal. Alternatively or additionally, the control unit increases the strength during one or more of the sessions. Further alternatively or additionally, the control unit increases the strength from episode to episode.

For some applications, so long as the episode is not resolved, the control unit repeats the application of the cardioversion signal in additional sessions (for some applications, increasing the signal strength from session to session or during one or more of the sessions, as described above), until one or more of following conditions is satisfied:

a certain maximum number of sessions is reached, e.g., 5 sessions;

a sensed ventricular response rate falls below a threshold value, such as 60 beats per minute (BPM), or by a threshold value from baseline, e.g., by at least 10% of baseline; and/or a sensed blood pressure falls below a threshold value, such as 75 mm Hg systolic, or by a threshold value from baseline, such as at least 10 mm Hg.

Upon satisfaction of one or more of these conditions, the control unit ceases to attempt cardioversion. For some applications, the control unit subsequently attempts cardioversion after a delay, such as 5 minutes.

In an embodiment of the present invention, upon detection of an episode of non-sinus atrial tachycardia, control unit 90 delays application of the cardioversion signal to allow for spontaneous resolution of the episode. The control unit applies the signal if the episode does not resolve during the delay. Typically, the delay is at least about 5 seconds, e.g., at least about 10, 20, or 30 seconds.

For some applications, control unit 90 is configured to perform the detection of the episode and make a determination that the episode has not resolved responsively to a signal generated by ECG monitor 92 and/or one or more of physiological sensors 94. Alternatively, the control unit receives a communication signal from an external episode detector, which is implanted in the subject or external thereto.

In an embodiment of the present invention, system 20 is configured to apply a signal to atrial tissue of patient 30, and to configure the signal to stimulate cardiac muscle tissue. Such stimulation in combination with application of the parasympathetic cardioversion signal generally helps terminate the episode of non-sinus atrial tachycardia. For some applications, control unit 90 configures the cardiac muscle signal to pace the atrium. For such applications, the control unit typically sets the cardiac muscle signal to have a conventional parameters for atrial pacing, such as a pulse duration of between about 0.2 and about 0.8 ms, and a pulse voltage of between about 0.1 and about 3 volts. For other applications, the control unit configures the cardiac muscle signal to have a greater strength than conventional atrial pacing pulses. For example, such parameters may include a pulse duration of at least about 0.5 ms, e.g., at least about 2 ms, 5 ms, or 10 ms, a frequency of between about 5 and about 50 Hz, e.g. about 20 Hz, and a voltage of between about 1 and about 10 volts.

For some applications, the cardiac muscle stimulation is delivered with the same set of one or more electrode devices 22 (or the same electrode device 22) as the parasympathetic stimulation, while for other applications, system 20 comprises separate sets of one or more electrode devices 22 for cardiac muscle stimulation and parasympathetic stimulation.

For some applications, the parasympathetic cardioversion signal is applied during the ventricular total refractory period, and the cardiac muscle signal is applied during another portion of the cardiac cycle, such as the ventricular relative refractory period. For some applications, the parasympathetic cardioversion signal is applied with a greater strength than the cardiac muscle signal. For example, the product of pulse width times frequency times current may be at least two times greater, e.g., at least three times greater. For some applications, this technique is used for treating conditions other than non-sinus atrial tachycardia, such as heart failure (either acute or chronic), arrhythmia prevention, acute myocardial ischemia, myocardial infraction, or myocardial hibernation.

In an embodiment of the present invention, control unit 90 is configured to apply atrial pacing when patient 30 is not experiencing an episode of non-sinus atrial tachycardia, and the parasympathetic cardioversion signal during such an episode. For some applications, the atrial pacing is delivered with the same set of one or more electrode devices 22 (or the same electrode device 22) as the parasympathetic stimulation, while for other applications, system 20 comprises separate sets of one or more electrode devices 22 for atrial pacing and parasympathetic stimulation.

In an embodiment of the present invention, system 20 comprises at least one ventricular electrode device. Control unit 90 is configured to drive the ventricular electrode device to apply ventricular pacing to a left ventricle 96 of patient 30 (FIG. 1). For some applications, the control unit is configured to sense the heart rate of patient 30, and apply the ventricular pacing whenever the heart rate falls below a threshold rate, e.g., 60 BPM. Alternatively or additionally, the control unit is configured to sense a P-R interval, and apply the ventricular pacing whenever the P-R interval exceeds a threshold value, such as 230 ms.

For other applications, the control unit is configured to apply the ventricular pacing whenever the control unit applies the parasympathetic cardioversion signal (i.e., not responsively to a drop in heart rate), in order to prevent or reduce an undesired drop in heart rate caused by the parasympathetic signal, and/or to maintain ventricular rhythm even during AV block caused by the parasympathetic cardioversion signal. For some applications, a calibration procedure is performed during implantation of system 20, in which a level of stimulation necessary for causing AV block is determined. During treatment with the system, whenever the system applies at least this level of stimulation, the system additionally applies ventricular pacing in order to maintain ventricular rhythm during the induced AV block. For example, the ventricular pacing may be applied at a rate of 70 BPM. For some applications, the system begins and terminates the ventricular pacing generally simultaneously with the application of the parasympathetic cardioversion signal, while for other applications the system begins the ventricular pacing before beginning application of the parasympathetic cardioversion signal, and/or terminates the ventricular pacing after terminating application of the parasympathetic cardioversion signal, such as several seconds before or after.

In an embodiment of the present invention, one or more stimulation parameters are set during an acute test calibration procedure during implantation of system 20, typically while the patient is under general anesthesia. Typically, the parameters are set so as to apply the minimal stimulation necessary to achieve a desired effect. For some applications, the stimulation parameters are set so as to achieve:

- a decrease in the atrial effective refractory period (AERP) by at least 5%, e.g., at least 10% from baseline;
- a reduction in systolic blood pressure, such as about 10 mm Hg;
- a reduction in heart rate, such as about 10% from baseline; and/or
- a prolongation of the P-R interval, such as at least 15 ms (this measurement is typically possible because the patient is generally in sinus rhythm during the calibration procedure).

Typically, this decrease is measured when the patient is not experiencing an episode of non-sinus atrial tachycardia.

For some applications, such an acute test is used to select patients who are expected to benefit most from treatment with system 20. During a surgical or percutaneous procedure, stimulation is applied and the acute effect on one or more physiological parameters is measured. The system is implanted only if a substantial improvement in the one or more physiological parameters is achieved. For example, the one or more physiological parameters and desired improvements may include:

- a reduction in AERP, such as at least a 5% reduction, e.g., at least a 10% reduction from baseline;
- a reduction in systolic blood pressure, such as at least 10 mm Hg from baseline;
- a reduction in heart rate, such as at least 10% from baseline; and/or
- a prolongation of the P-R interval, such as at least 15 seconds.

Typically, these parameters are measured when the patient is not experiencing an episode of non-sinus atrial tachycardia.

Alternatively, the acute selection test is performed during an induced or naturally-occurring episode of non-sinus atrial tachycardia, and the test is considered to be successful if the system terminates the episode. For some applications, the acute test is performed by stimulating one or more parasympathetic atrial sites of the patient.

For some applications, in addition to setting the effective stimulation level, the acute test is utilized to ascertain the maximum safe dose of stimulation for the patient. For example, the maximum safe dose may be defined as a level of stimulation that does not reduce systolic blood pressure below a threshold value (e.g., 80 mmHg), cause complete AV block, and/or result in ventricular capture (depolarization of the ventricle in direct response to the stimulation). Typically, the test is performed when the patient is not experiencing an episode of the non-sinus atrial tachycardia.

For some applications, these calibration techniques are used for treating other conditions, such as heart failure (acute or chronic), arrhythmia prevention, arrhythmia termination, acute myocardial ischemia, myocardial infarction, myocardial hibernation, another cardiac condition, or high blood pressure.

In an embodiment of the present invention, one or more of electrode devices 22 are configured to be placed at an intravascular location, and to transvascularly apply stimulation to a site containing parasympathetic nervous tissue. For some application, techniques for intravascular stimulation are used that are described in U.S. Pat. No. 6,292,695 to Webster, Jr. et al., U.S. Pat. RE38,705 to Hill et al., U.S. Pat. No. 5,170,802 to Mehra, the above-referenced article by Goldberger J J et al. (1999), US Statutory Invention Registration H1,905 to Hill, U.S. Pat. No. 5,224,491 to Mehra, U.S. Pat. No. 6,564,096 to Mest, U.S. Pat. Nos. 6,073,048 and 6,985,774 to Kieval et al., and/or U.S. Pat. No. 6,934,583 to Weinberg et al., all of which are incorporated herein by reference.

In an embodiment of the present invention, a system is provided that comprises a housing, which comprises a control unit and/or circuitry contained within the housing, and one or more electrodes. The housing is configured to be positioned at an intravascular site, typically an intravascular venous site, such as the superior vena cava. The housing is typically implanted using a catheterization procedure. For some applications, the housing comprises a power source, such as a battery or capacitor. For some applications, the control unit is configured to receive power and/or parameters of the stimulation transmitted from a non-implantable transmitter located outside the body of the subject. For some applications, a non-implantable monitor is configured to perform the detection of the episode.

For some applications, the techniques of this embodiment are practiced in combination with the techniques described in the above-referenced U.S. Pat. No. 7,082,336 to Ransbury et al.

In an embodiment, the system comprises an external controller, which is configured to be placed outside the body of patient 30. For some applications, the controller is configured to wirelessly transmit power to housing, such as electromagnetically or by induction. For some applications, the controller comprises or is coupled to an external monitor for detecting an episode of non-sinus atrial tachycardia, such as AF or atrial flutter. Upon such detection, the controller drives the housing to apply a parasympathetic cardioversion signal, as described hereinabove. Alternatively or additionally, patient 30 activates the system upon feeling symptoms associates with an episode. For example, the patient may touch the controller, or a wand coupled to the controller, to the surface of the body near the heart.

Reference is again made to FIG. 1. In an embodiment of the present invention, system 20 comprises a blood pressure sensor 94. Control unit 90 uses blood pressure sensor 94, either alone or in conjunction with other sensors described hereinabove, to detect an episode of non-sinus atrial tachycardia. For example, the control unit may detect an episode responsively to a change in a blood pressure curve pattern, or a disassociation between a blood pressure curve and the ECG.

In an embodiment of the present invention, control unit 90 uses the measured blood pressure to assess the efficacy of the parasympathetic cardioversion signal, for example, by detecting whether the signal has resolved blood pressure curve irregularities, or a disassociation between a blood pressure curve and the ECG. For some applications, the control unit sets one or more parameters of the signal to a level effective to induce a certain reduction in blood pressure.

In an embodiment of the present invention, a system for treating non-sinus atrial tachycardia comprises blood pressure-reducing functionality and a control unit coupled thereto. Upon the detection of episode of non-sinus atrial tachycardia, the control unit drives the functionality to cause a reduction in blood pressure of patient 30 sufficient to induce atrial cardioversion. For some applications, this technique is used alone, while for other applications, this technique is used in combination with the parasympathetic cardioversion techniques described herein. Techniques for reducing blood pressure include, but are not limited to:

- electrical stimulation of a parasympathetic site, such as described herein;
- electrical stimulation of one or more baroreceptors at sites such as the carotid bifurcation or jugular vein. For some application, techniques are used that are described in U.S. Pat. Nos. 6,073,048 and/or 6,985,774 to Kieval et al.;
- reduction of the forward activity of a ventricular assist device;
- activation of a control valve implanted at a venous site for obstruction of blood flow; and
- administration, such as by infusion, of a blood pressure-lowering drug, such as nitroglycerine or adenosine.

For some applications, the control unit is configured to drive the blood pressure-reducing functionality to maintain the reduced level of blood pressure for a certain period of time, such as at least 5 seconds, e.g., at least 10 seconds, at least 20 seconds, or at least 30 seconds.

For some applications, the system comprises a blood pressure sensor, and the control unit drives the blood pressure-reducing functionality to reduce the blood pressure to a target level responsively to the blood pressure sensed by the blood pressure sensor. For some applications, this reduced level of blood pressure is maintained for a certain period of time, such as at least 5 seconds, e.g., at least 10 seconds, at least 20 seconds, or at least 30 seconds.

For some applications, the system is configured to treat an episode of non-sinus atrial tachycardia, in combination with techniques described herein. Alternatively or additionally, the system is configured to perform ventricular cardioversion, or to treat heart failure, another atrial or ventricular arrhythmia, an inflammatory condition, another condition mentioned in the references in the Background or the Invention section or in the applications and patents incorporated assigned to the assignee of the present application and incorporated hereinbelow by reference.

In an embodiment of the present invention, a method for treating a subject at risk of suffering from atrial fibrillation (AF) comprises:

reducing the risk of an occurrence of an episode of the AF by applying an electrical current to a vagus nerve or other parasympathetic tissue that innervates the heart of the subject, such as by using the techniques described in the above-referenced U.S. patent application Ser. No. 11/657,784, filed Jan. 24, 2007, entitled, "Techniques for prevention of atrial fibrillation";

upon the occurrence of the episode, attempting to induce cardioversion using one or more of the techniques described herein.

In an embodiment of the present invention, parasympathetic tissue is stimulated chemically, such as to induce cardioversion of an episode of non-sinus atrial tachycardia. For example, a pump may release a bolus to a peripheral vein upon detection of the episode. The substance may include, for example, acetylcholine, nitroglycerine, or adenosine. Typically, a reservoir is implanted elsewhere in the body.

In an embodiment of the present invention, control unit 90 drives electrode device 22 to apply an electrical current to vagus nerve 24, and drives pacemaker 42 to apply pacing signals to heart 28. The control unit configures the current and the pacing signals to treat the episode of non-sinus atrial tachycardia of patient 30. For some applications, the control unit configures pacemaker 42 to apply the pacing signals with pulse repetition intervals having a duration of between about 50% and about 200% of an atrial refractory period of patient 30 (e.g., between about 15 ms and about 190 ms), so as to treat the episode of non-sinus atrial tachycardia. For some applications, the control unit configures the vagal stimulation current to modulate the atrial refractory period. For some applications, the control unit modulates one or more parameters of the vagal stimulation current and/or of the pacing signal, such as on/off time, amplitude, number of pulses, pulse repetition interval (i.e., the interval between the leading edges of two consecutive pulses), or other parameters described herein.

For some applications, control unit 90 is adapted to distinguish between the episode of non-sinus atrial tachycardia and NSR, generally by analyzing an ECG signal generated by ECG monitor 92. In order to detect rapid atrial activity indicative of the episode of non-sinus atrial tachycardia, the analysis may include one or more of the following:

- P-wave analysis;
- analysis of ventricular response rate and/or ventricular response variability;
- sensed pressure, such as atrial pressure, sensed venous pressure, and/or sensed arterial pressure;
- the relationship(s) between one or more of the sensed pressures and sensed ventricular contractions (in the case of arterial pressure, such relationship is an indication of pulse deficit); and/or
- analysis of the duration of the isoelectrical segment of the ECG, optionally using the technique described in the above-cited article by Wijffels et al., entitled, "Atrial fibrillation begets atrial fibrillation." A duration greater than a first threshold value is typically indicative of NSR, while a duration less than a second threshold value, the second threshold value less than or equal to the first threshold value, is typically indicative of AF.

Control unit 90 itself may perform this analysis, or it may transmit data for analysis by an external processor (not shown).

Typically, system 20 is programmable by a physician, such as by using an external console wirelessly in communication with control unit 90. The system typically provides notification of various occurrences, such as the initiation of an episode of non-sinus atrial tachycardia, cardioversion, or a mechanical failure. The system may provide such notifications by various means, including generating a tone, vibrating, and/or wirelessly communicating with a local or remote receiver, such as one located at a medical facility.

In an embodiment of the present invention, control unit 90 drives electrode device 22 to apply signals to vagus nerve 24, and configures the signals so as to restore NSR, i.e., to induce cardioversion. According to a first approach for restoring NSR, the configuration includes repeatedly changing parameters of the stimulation. The parameters changed may include one or more of the following:

- intensity of stimulation (amplitude and/or frequency)—the strength of the stimulation is switched between stronger and weaker intensities;
- on/off—the stimulation is configured to switch between applying stimulation and not applying stimulation, and/or a duration of an "on" period and/or an "off" period of the stimulation is varied;
- pulse width of the stimulation; and/or induce/block—the stimulation is configured to switch between inducing action potentials in the vagus nerve and blocking action potentials in the vagus nerve.

Typically, control unit 90 cycles between application of the different parameters at a rate of between about the duration of one heart beat and about 30 seconds. For some applications, the control unit performs the switching according to a predetermined pattern. For other applications, the control unit performs the switching randomly, with a typical interval between changes of between about 500 milliseconds and about 30 seconds.

Such switching of the stimulation is believed by the inventors to cause fluctuations in the atrial effective refractory period (AERP), thereby breaking reentry cycles and restoring synchronization and NSR. The inventors hypothesize that although the effect of vagal stimulation on the atria is generally heterogeneous in nature (not all areas of the atria receive the same stimulus), rapid switching of the stimulation, i.e., the application of heterogeneous stimuli, causes an overall atrial response that is more homogenous. The inventors further hypothesize that such atrial cell synchronization is due in part to: (a) more frequent activation of atrial cells because of the reduced refractory period caused by the vagal stimulation, and/or (b) the breaking of re-entry circuits during the brief periods when weak, blocking, or no vagal stimulation is applied.

According to a second approach for restoring NSR, control unit 90:
 during a first period, typically having a duration between about 500 milliseconds and about 30 seconds, (a) paces the heart using conventional pacing techniques, such as by driving conventional pacemaker 42 to apply pacing signals to the heart, e.g., to the right atrium, right ventricle, or both ventricles, and, simultaneously, (b) configures the signals applied to the vagus nerve to provide generally constant vagal stimulation, i.e., without varying parameters of the stimulation, with a high intensity. Pacing of the heart is generally necessary because such high-intensity vagal stimulation would otherwise severely slow the heart rate; and
 during a second period, suddenly ceases vagal stimulation. Such sudden cessation generally destabilizes the atrial cells, resulting in a return to NSR. The destabilization may be thought of as analogous to that achieved by conventional electrical cardioversion. The pacing is also generally terminated during the second period, typically simultaneously with, or up to about 30 seconds after, cessation of vagal stimulation. Alternatively, the pacing is terminated upon restoration of atrial activity.

The control unit may be configured to repeat this stimulation/pacing—sudden cessation cycle, if necessary to restore NSR.

A third approach is typically appropriate for treating AF principally caused by heightened adrenergic tone. When atrial fibrillation is induced by adrenergic tone, vagal stimulation generally reduces the net adrenergic effect by slowing the heart rate and by antagonizing the adrenergic system. According to this third approach, control unit 90 drives electrode device 22 to apply signals to vagus nerve 24, and configures the signals to apply substantially constant vagal stimulation, i.e., without varying parameters of the stimulation, so as to restore NSR. In this approach, the control unit typically does not use feedback in order to vary the parameters of stimulation. Parameters typically appropriate for such stimulation include: (a) application of a single pulse or a single burst of pulses each heart beat, (b) a pulse width of between about 0.5 ms and about 1.5 ms, and (c) a PPT of between about 1 and about 10. The amplitude of the applied signal is typically dependant upon the specific electrode device used for the treatment.

For all three of these approaches, the control unit may be configured to apply the cardioversion treatment: (a) upon detection of the episode of non-sinus atrial tachycardia, (b) upon receiving an operator command, such as from a health care worker, or (c) at some other time. For some applications, the control unit applies the treatment at a certain time of day and/or when a patient motion signal received from accelerometer 39 indicates that the patient is at rest.

FIG. 4 is a flow chart that schematically illustrates a method for determining and applying an appropriate AF treatment based on a countdown, in accordance with an embodiment of the present invention. In this embodiment, system 20 additionally comprises a timer 43, which optionally is integrated in software of control unit 90 (FIG. 1). Alternatively, the functions of timer 43 may be implemented in circuitry of control unit 90. At an AF monitoring step 200, system 20 monitors patient 30 for indications of AF, such as by using one or more of the AF detection techniques described hereinabove. So long as AF is not detected at an AF check step 202, the method returns to step 200. On the other hand, if AF is detected, control unit 90 records the time of initiation of the AF and optionally generates a notification signal, at a recording and notification step 204.

The control unit is typically adapted to report the recorded time of AF initiation and/or countdown time upon interrogation by a physician. If the patient seeks medical care after generation of the notification signal in step 204, the physician typically considers the recorded AF initiation time when determining the appropriate therapy. If the physician opts to attempt conventional cardioversion, the physician may reset the system to resume monitoring for AF at step 200. Alternatively, the physician may opt to allow the device to continue its therapeutic course at step 206, as follows.

The control unit activates timer 43 to begin a countdown, at a countdown step 206. The countdown typically has a duration from the detection of AF of between about 24 and 54 hours, such as 48 hours. During the countdown, system 20 typically attempts to restore NSR, using the cardioversion techniques and system described herein, or other methods and system known in the art, such as ICD 41. After attempting to restore NSR, at a success check step 210, the system determines whether NSR has been successfully restored and maintained, such as by using one or more of the AF detection techniques described hereinabove. If NSR has been restored, the system typically generates a notification signal to the patient and/or healthcare worker, at a notification generation step 212. The system then resumes monitoring the patient for subsequent AF, at step 200.

On the other hand, if NSR has not been restored, then the system checks whether the countdown has been completed, at a countdown check step 216. If the countdown has not been completed, the system again attempts cardioversion, at step 208. For some applications, the system is configured to pause between cardioversion attempts, and/or to make only a certain number of cardioversion attempts, typically based on programmed parameters and/or physiological parameters measured in real time. If, on the other hand, the countdown has concluded, at an AF maintenance step 216 the system attempts to maintain AF, typically using AF maintenance techniques described in U.S. patent application Ser. No. 10/560,654, filed May 1, 2006, which published as US Patent Application Publication 2006/0271115. By minimizing or preventing undesired spontaneous transitions into NSR, the system may reduce the risk of thromboembolic events, such as stroke. AF maintenance typically continues until a physician intervenes by signaling the system to terminate maintenance, at an AF maintenance termination step 218.

For some applications, system 20 is used with this countdown method in order to implement a set of clinical guidelines for treatment of AF. For example, the above-cited ACC/AHA/ESC practice guidelines for AF suggest that immediate cardioversion be attempted when AF has been present for less than 48 hours, but that the patient receive anticoagulation therapy for three to four weeks before cardioversion is attempted if the AF has been present for more than 48 hours. Such an anticoagulation period is also recommended when the duration of AF is unknown, for example, because the patient may have been asymptomatic for a period of time after initiation of AF. The use of this countdown method generally eliminates this unknown, thereby sometimes allowing beneficial cardioversion to be performed immediately rather than after three to four weeks of an anticoagulation drug regimen.

In an embodiment of the present invention, means are employed for avoiding bradycardia, which may be induced in response to application of some of the techniques described herein. Such means include, but are not limited to:

Applying stimulation only when the heart rate of the subject is greater than a minimum threshold, e.g., 60 beats per minute;

In the event that the heart rate drops below a threshold rate, e.g., 60 beats per minute, the heart is paced using conventional pacing techniques, such as by driving conventional pacemaker 42 to apply pacing signals to the heart, e.g., to the right atrium, right ventricle, or both ventricles, in order to keep the heart rate at or above the threshold value; and Monitoring heart rate after applying stimulation. Upon detection that heart rate has fallen below a threshold rate, e.g., 60 beats per minute, during the following application of stimulation one or more parameters of the stimulation are adjusted so as to reduce the strength of the stimulation. For some applications, this technique is applied periodically or continuously while applying stimulation.

For many of the applications of vagal stimulation described herein, electrode device 22 typically comprises one or more electrodes, such as monopolar, bipolar or tripolar electrodes. Electrode device 22 is typically placed: (a) around vagus nerve 24, (b) around vagus nerve 24 and the carotid artery (configuration not shown), (c) inside the carotid artery in a position suitable for vagal stimulation (configuration not shown), (d) around the thoracic vagus nerve trunk, or (e) at an atrial site. Depending on the particular application, one or more electrode devices 22 may be positioned to stimulate the left or right vagus nerve, either above or below the cardiac branch bifurcation. For some applications, the electrodes comprise cuff electrodes, ring electrodes, and/or point electrodes. Typically, the electrodes stimulate the nerve without coming in direct contact therewith, by applying an electrical field to the nerve. Alternatively, the electrodes stimulate the nerve by coming in direct contact therewith. For applications in which excitatory signals are applied to vagus nerve 24 (as opposed to inhibiting signals), control unit 90 typically configures the signals to induce the propagation of efferent nerve impulses towards heart 28. For some applications in which electrode device 22 is applied to tissue other than a longitudinal nerve, the electrode device is coupled to the tissue using techniques used by known pacemaker leads.

In some embodiments of the present invention, when configuring vagal stimulation to induce the propagation of efferent nerve impulses towards heart 28, control unit 90 drives electrode device 22 to (a) apply signals to induce the propagation of efferent nerve impulses towards heart 28, and (b) suppress artificially-induced afferent nerve impulses towards a brain of the patient, in order to minimize unintended side effects of the signal application.

In some embodiments of the present invention, techniques described herein are practiced in combination with techniques described in U.S. patent application Ser. No. 10/560,654, filed May 1, 2006, which published as US Patent Application Publication 2006/0271115. For example, electrode device 22 may utilize techniques described therein with reference to FIGS. 3A-C and/or 4, and/or smaller-to-larger diameter fiber recruitment may be achieved using techniques described therein with reference to FIG. 5.

For some applications, control unit 90 is adapted to receive feedback from one or more of the electrodes in electrode device 22, and to regulate the signals applied to the electrode device responsive thereto. For example, control unit 90 may analyze amplitudes of various peaks in a compound action potential (CAP) signal recorded by the electrodes, in order to determine a relative proportion of stimulated larger fibers (having faster conduction velocities) to smaller fibers (having slower conduction velocities). Alternatively or additionally, control unit 90 analyzes an area of the CAP, in order to determine an overall effect of the stimulation. In an embodiment, the feedback is received by electrodes other than those used to apply signals to the nerve.

Optionally, the stimulation applied by vagal stimulation system 20 is applied in conjunction with or separately from stimulation of sympathetic nerves innervating the heart. For example, vagal inhibition described herein and/or periods of non-stimulation of the vagus nerve described herein may be replaced or supplemented by excitation of sympathetic nerves. Such sympathetic stimulation can be applied using techniques of smaller-to-larger diameter fiber recruitment, as described herein, or other nerve stimulation techniques known in the art.

Figure 5:
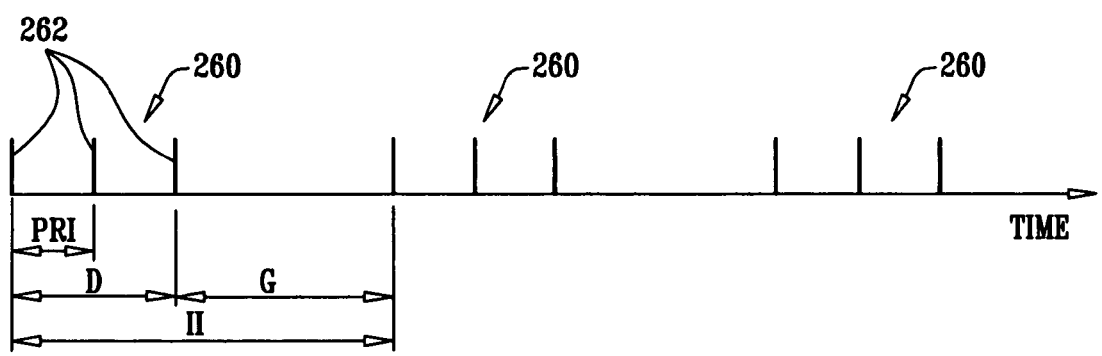
FIG. 5 is a schematic illustration of a series of bursts applied by the system of FIG. 1, in accordance with an embodiment of the present invention.

Reference is made to FIG. 5, which is a schematic illustration of a series of bursts 260, in accordance with an embodiment of the present invention. Control unit 90 is configured to drive electrode device 26 to apply stimulation, such as for resolving an episode of non-sinus atrial tachycardia, as described herein, in the series of bursts 260, at least one of which bursts includes a plurality of pulses 262, such as at least three pulses 262. Control unit 90 configures:

(a) a pulse repetition interval (PRI) within each of multipulse bursts 260 (i.e., the time from the initiation of a pulse to the initiation of the following pulse within the same burst) to be on average at least 20 ms, such as at least 30 ms, e.g., at least 50 ms or at least 75 ms, and (b) an interburst interval (II) (i.e., the time from the initiation of a burst to the initiation of the following burst) to be at least a multiple M times the burst duration D. Multiple M is typically at least 1.5 times the burst duration D, such as at least 2 times the burst duration, e.g., at least 3 or 4 times the burst duration. (Burst duration D is the time from the initiation of the first pulse within a burst to the conclusion of the last pulse within the burst.)

In other words, burst duration D is less than a percentage P of interburst interval II, such as less than 75%, e.g., less than 67%, 50%, or 33% of the interval. For some applications, the PRI varies within a given burst, in which case the control unit sets the PRI to be on average at least 20 ms, such as at least 30 ms, e.g., at least 50 ms or at least 75 ms. For other applications, the PRI does not vary within a given burst (it being understood that for these applications, the "average PRI" and the PRI "on average," including as used in the claims, is equivalent to the PRI; in other words, the terms "average PRI" and the PRI "on average" include within their scope both (a) embodiments with a constant PRI within a given burst, and (b) embodiments with a PRI that varies within a given burst).

Typically, each burst 260 includes between two and 14 pulses 262, e.g., between two and six pulses, and the pulse duration (or average pulse duration) is between about 0.1 and about 4 ms, such as between about 100 microseconds and about 2.5 ms, e.g., about 1 ms. Typically, control unit 90 sets the interburst interval II to be less than 10 seconds. For some applications, control unit 90 is configured to set the interburst interval II to be between 400 ms and 1500 ms, such as between 750 ms and 1500 ms. Typically, control unit 90 sets an interburst gap G between a conclusion of each burst 260 and an initiation of the following burst 260 to have a duration greater than the PRI. For some applications, the duration of the interburst gap G is at least 1.5 times the PRI, such as at least 2 times the PRI, at least 3 times the PRI, or at least 4 times the PRI.

Although the control unit typically withholds applying current during the periods between bursts and between pulses, it is to be understood that the scope of the present invention includes applying a low level of current during such periods, such as less than 50% of the current applied during the "on" periods, e.g., less than 20% or less than 5%. Such a low level of current is hypothesized to have a different, significantly lower, or a minimal physiological effect on the subject. For some applications, control unit 90 is configured to apply an interburst current during at least a portion of interburst gap G, and to set the interburst current on average to be less than 50% (e.g., less than 20%) of the current applied on average during the burst immediately preceding the gap. For some applications, control unit 90 is configured to apply an interpulse current to the site during at least a portion of the time that the pulses of bursts 260 are not being applied, and to set the interpulse current on average to be less than 50% (e.g., less than 20%) of the current applied on average during bursts 260.

For some applications, the control unit is configured to synchronize the bursts with a feature of the cardiac cycle of the subject. For example, each of the bursts may commence after a delay after a detected R-wave, P-wave, or other feature of an ECG. For these applications, one burst is typically applied per heart beat, so that the interburst interval II equals the R-R interval, or a sum of one or more sequential R-R intervals of the subject. Alternatively, for some applications, the control unit is configured to synchronize the bursts with other physiological activity of the subject, such as respiration, muscle contractions, or spontaneous nerve activity.

In an embodiment of the present invention, the control unit sets the PRI to at least 75% of a maximum possible PRI for a given interburst interval II (such as the R-R interval of the subject), desired percentage P, and desired PPT. For some applications, the following equation is used to determine the maximum possible PRI:

$$PRI = II * P / (PPT - 1) \quad \text{(Equation 1)}$$

For example, if the II is 900 ms, percentage P is 33.3%, and the desired PPT is 4 pulses, the maximum possible PRI would be 900 ms*33.3%/(4−1)=100 ms, and the control unit would set the actual PRI to be at least 75 ms. For some applications, control unit 90 uses this equation to determine the PRI, such as in real time or periodically, while for other applications this equation is used to produce a look-up table which is stored in the control unit. For still other applications, this equation is used to configure the control unit. For some applications, multiple M is a constant, which is stored in control unit 90, while for other applications, control unit 90 adjusts M during operation, such as responsively to one or more sensed physiological values, or based on the time of day, for example. It is noted that Equation 1 assumes that the pulse width of the pulses does not contribute meaningfully to burst duration D. Modifications to Equation 1 to accommodate longer pulse widths will be evident to those skilled in the art.

For some applications, when using Equation 1, a maximum value is set for the PRI, such as between 175 and 225, e.g., about 200, and the PRI is not allowed to exceed this maximum value regardless of the result of Equation 1.

Reference is made to FIGS. 6A-B, which are schematic perspective and cross-sectional illustrations, respectively, of a tracheal stimulation system, in accordance with an embodiment of the present invention. The tracheal stimulation system comprises a tracheal electrode device 300, which is configured to be placed within a trachea 310 of a subject, and to apply electrical stimulation of a thoracic vagus nerve through the wall of the trachea.

Tracheal electrode device 300 comprises one or more electrodes 320 positioned on a surface of the device that is configured to come in contact with the inner surface of trachea 310. For some applications, tracheal electrode device 300 is positioned such that electrodes 320 are positioned between about 2 and about 10 cm (e.g., between about 2 and about 6 cm) above a carina 312 of the trachea. The tracheal stimulation system comprises circuitry 322, which is configured to drive the electrodes to apply the electrical stimulation. For some applications, circuitry 322 comprises a power source, such as a battery (optionally a rechargeable battery). For some applications, circuitry 322 is configured to receive a communication signal from outside a body of the subject, such electromagnetically, by induction, or by ultrasound energy. The signal includes data (e.g., one or more parameters of the stimulation) and/or power for recharging the power source or directly powering the stimulation.

Tracheal electrode device 300 typically comprises an attachment element for coupling the device to the inner surface of the trachea. For some applications, the attachment element comprises a band 324, which is typically adjustable to the size of the trachea. Alternatively, the device is configured to exert an outward pressure on the wall of the trachea that is sufficient to hold the device in place, in which case the device typically does not extend entirely around the trachea. Alternatively or additionally, the attachment element comprises one or more coupling elements that are configured to partially or fully penetrate the wall of the trachea, in order to couple the device to the wall.

For some applications, the electrode device is configured and placed in the trachea to stimulate one of the right or left thoracic vagus nerves. For these applications, electrodes 320 are distributed over a circumferential portion of the electrode device that is brought into a vicinity of the selected thoracic vagus nerve when the electrode device is appropriately positioned in the trachea. For other applications, the electrode device is configured and placed in the trachea to stimulate both the right and left thoracic vagus nerves, in which case the electrodes are distributed over two circumferential portions of the electrode device that are brought into respective vicinities of the right and left thoracic vagus nerves, or over the entire circumference of the electrode device.

Figure 7:
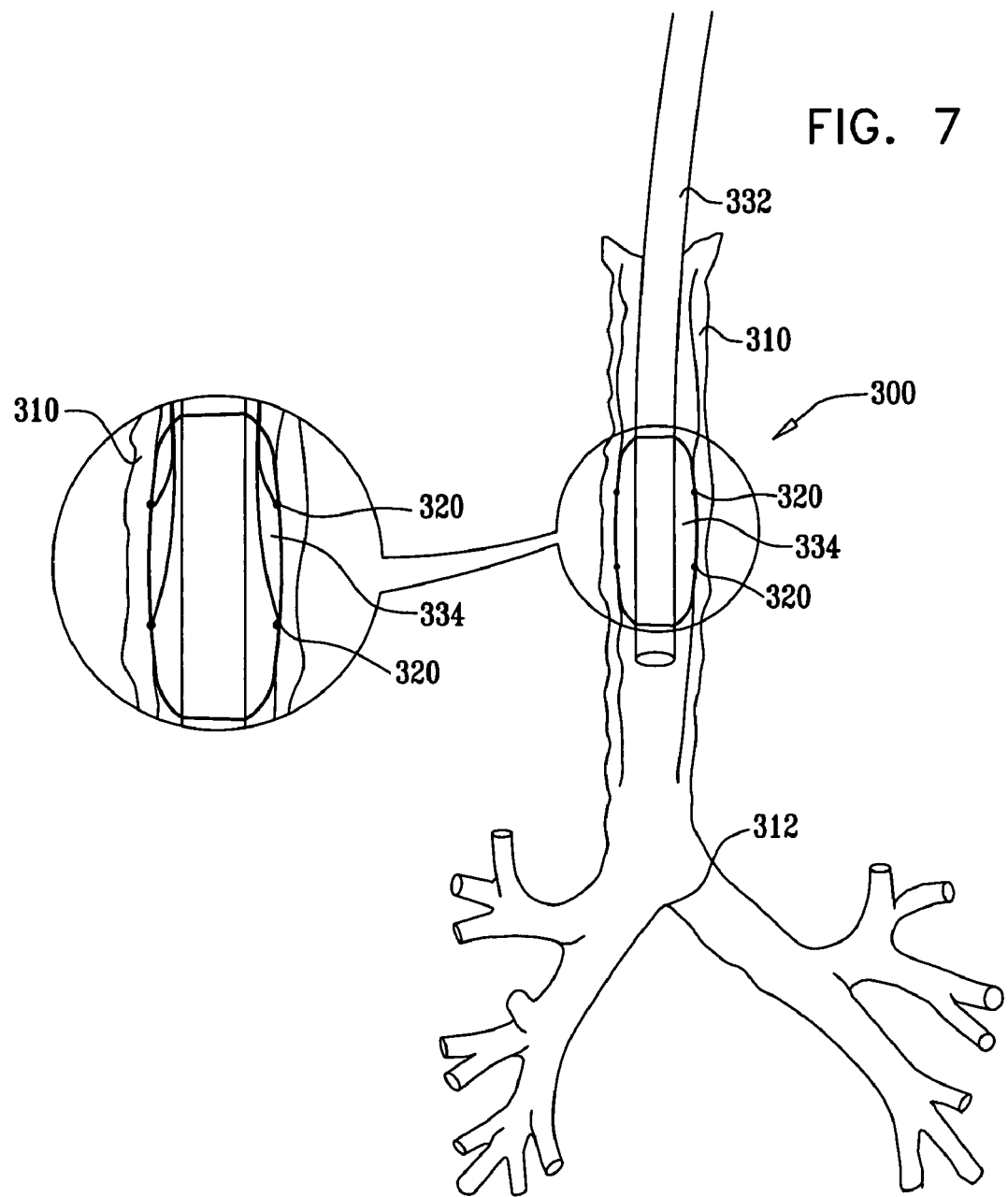
FIG. 7 is a schematic illustration of another tracheal stimulation system, in accordance with an embodiment of the present invention.

Reference is made to FIG. 7, which is a schematic illustration of another tracheal stimulation system, in accordance with an embodiment of the present invention. Except as described below, this tracheal stimulation system is generally similar to the tracheal stimulation system described hereinabove with reference to FIGS. 6A-B. The tracheal stimulation system comprises a tracheal electrode device 330, which is configured to be temporarily placed within trachea 310. The device comprises a positioning tool that holds the device in place. For some applications, the positioning tool comprises a tube 332, such as an endotracheal tube.

For some applications, tracheal electrode device 330 comprises an inflatable element 334 (e.g., a balloon), and electrodes 320 are positioned on an outer surface of the inflatable element. Inflatable element 334 is typically placed around all or a portion of the positioning tool, e.g., tube 332. Alternatively or additionally, the electrodes are positioned directly on an outer surface of the positioning tool, e.g., tube 332 (configuration not shown). Further alternatively or additionally, the tube is shaped so as define one or more canals through which the electrodes are advanced to come in contact with the tracheal tissue (configuration not shown).

The tracheal stimulation system comprises circuitry, which, for some applications, is contained within the positioning tool (such as within tube 332, e.g., in a vicinity of electrodes 320). For other applications, the circuitry is positioned outside the body of the subject, and electrically coupled to electrodes 320 over leads that pass through or along tube 332.

This embodiment thus enables vagal stimulation to be applied to intubated patients without the need to perform an additional invasive procedure. The tracheal stimulation system thus may be used, for example, for intraoperative vagal stimulation during general anesthesia, vagal stimulation for the unconscious, comatose or brain dead, and vagal stimulation for patients on ventilatory support.

In an embodiment of the present invention, an esophageal stimulation system is provided. The esophageal stimulation system comprises an esophageal electrode device, which is configured to be placed within an esophagus of a subject, and to apply electrical stimulation of a thoracic and/or abdominal portion of the vagus nerve through the wall of the esophagus. In this area, the left and right vagus nerves interconnect to form a plexus.

The esophageal electrode device comprises one or more electrodes positioned on a surface of the device that is configured to come in contact with the inner surface of the esophagus. For some applications, the electrodes are positioned above a lower esophageal sphincter (LES), such as between about 2 and about 10 cm above the LES. The esophageal stimulation system comprises circuitry, which is configured to drive the electrodes to apply the electrical stimulation. For some applications, the circuitry comprises a power source, such as a battery (optionally a rechargeable battery). For some applications, the circuitry is configured to receive a communication signal from outside a body of the subject, such electromagnetically, by induction, or by ultrasound energy. The signal includes data (e.g., one or more parameters of the stimulation) and/or power for recharging the power source or directly powering the stimulation.

The esophageal electrode device typically comprises an attachment element for coupling the device to the inner surface of the esophagus, such as described hereinabove with reference to FIGS. 6A-B for tracheal electrode device 300, mutatis mutandis.

For some applications, the esophageal electrode device is configured to be temporarily placed within the esophagus. The device comprises a positioning tool that holds the device in place. For some applications, the positioning tool comprises a tube, such as a nasogastric tube.

For some applications, the esophageal electrode device comprises an inflatable element (e.g., a balloon), and the electrodes are positioned on an outer surface of the inflatable element. The inflatable element is typically placed around all or a portion of the positioning tool, e.g., the tube. Alternatively or additionally, the electrodes are positioned directly on an outer surface of the positioning tool, e.g., the tube. Further alternatively or additionally, the tube is shaped so as define one or more canals through which the electrodes are advanced to come in contact with the esophageal tissue This embodiment enables parasympathetic stimulation to be applied to patients intubated with a nasogastric tube without the need to perform an additional invasive procedure. The esophageal stimulation system thus may be used, for example, for intraoperative vagal stimulation during general anesthesia, vagal stimulation for the unconscious, comatose or brain dead, and vagal stimulation for patients in the postoperative period following abdominal operations.

For some applications, the esophageal stimulation system utilizes apparatus and/or techniques described hereinabove with reference to FIGS. 6A-B and/or 7, mutatis mutandis.

For some applications, the tracheal stimulation systems described hereinabove with reference to FIGS. 6A-B and 7, and the esophageal stimulation system described hereinabove are used for applying the parasympathetic cardioversion stimulation signal described hereinabove. Alternatively, these systems are used to treat another condition of the subject, to facilitate a surgical procedure, or to reduce the side effects of such a procedure. Such stimulation may, for example, reduce pain, increase consciousness level, reduce inflammation and inflammatory responses, slow the heart rate, reduce the blood pressure, increase gastrointestinal motility, induce internal secretions (such as induce pancreatic exocrine release of enzymes), and/or reduce peripheral resistance. For some applications, vagal stimulation is applied in order to stimulate the vagus nerve, while for other applications, the stimulation is configured to inhibit the vagus nerve (for example, the stimulation may be configured to have a high frequency, e.g., at least about 50 Hz). When the stimulation is applied in order to inhibit the vagus nerve, the stimulation may also dilate the bronchial tree, temporary paralyze the GI tract, divert blood flow away from the GI system, and/or reduce portal vein pressure.

For some applications, the stimulation techniques described herein are used to stimulate the parasympathetic system for therapeutic purposes other than non-sinus atrial tachycardia, such as treatment of heart failure, prevention of atrial fibrillation, treatment and/or prevention of ventricular arrhythmia, treatment of high blood pressure, or other conditions described in the references incorporated herein by reference in the Background of the Invention or the applications assigned to the assignee of the present application listed hereinbelow.

Although some embodiments of the present invention are described herein with respect to applying a designated electrical current to tissue of a patient, this is to be understood in the specification and in the claims as including creating a designated voltage drop between two or more electrodes.

In some embodiments, techniques described herein are applied in combination with techniques described in the above-mentioned U.S. Provisional Patent Application 60/478,576.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

U.S. patent application Ser. No. 10/205,474, filed Jul. 24, 2002, entitled, "Electrode assembly for nerve control," which published as US Patent Application Publication 2003/0050677

U.S. Provisional Patent Application 60/383,157 to Ayal et al., filed May 23, 2002, entitled, "Inverse recruitment for autonomic nerve systems"

U.S. patent application Ser. No. 10/205,475, filed Jul. 24, 2002, entitled, "Selective nerve fiber stimulation for treating heart conditions," which published as US Patent Application Publication 2003/0045909

PCT Patent Application PCT/IL02/00068, filed Jan. 23, 2002, entitled, "Treatment of disorders by unidirectional nerve stimulation," which published as PCT Publication WO 03/018113, and U.S. patent application Ser. No. 10/488,334, filed Feb. 27, 2004, in the US National Phase thereof U.S. patent application Ser. No. 09/944,913, filed Aug. 31, 2001, entitled, "Treatment of disorders by unidirectional nerve stimulation," which issued as U.S. Pat. No. 6,684,105

U.S. patent application Ser. No. 10/461,696, filed Jun. 13, 2003, entitled, "Vagal stimulation for anti-embolic therapy," which published as US Patent Application Publication 2004/0254612

PCT Patent Application PCT/IL03/00430, filed May 23, 2003, entitled, "Electrode assembly for nerve control," which published as PCT Publication WO 03/099373

PCT Patent Application PCT/IL03/00431, filed May 23, 2003, entitled, "Selective nerve fiber stimulation for treating heart conditions," which published as PCT Publication WO 03/099377

U.S. patent application Ser. No. 10/719,659, filed Nov. 20, 2003, entitled, "Selective nerve fiber stimulation for treating heart conditions," which published as US Patent Application Publication 2004/0193231

PCT Patent Application PCT/IL04/00440, filed May 23, 2004, entitled, "Selective nerve fiber stimulation for treating heart conditions," which published as PCT Publication WO 04/103455

PCT Patent Application PCT/IL04/000496, filed Jun. 10, 2004, entitled, "Vagal stimulation for anti-embolic therapy," which published as PCT Publication WO 04/110550

U.S. patent application Ser. No. 10/866,601, filed Jun. 10, 2004, entitled, "Applications of vagal stimulation," which published as US Patent Application Publication 2005/0065553

PCT Patent Application PCT/IL04/000495, filed Jun. 10, 2004, entitled, "Applications of vagal stimulation," which published as PCT Publication WO 04/110549

U.S. patent application Ser. No. 11/022,011, filed Dec. 22, 2004, entitled, "Construction of electrode assembly for nerve control," which published as US Patent Application Publication 2006/0136024

U.S. patent application Ser. No. 11/062,324, filed Feb. 18, 2005, entitled, "Techniques for applying, calibrating, and controlling nerve fiber stimulation," which published as US Patent Application Publication 2005/0197675

U.S. patent application Ser. No. 11/064,446, filed Feb. 22, 2005, entitled, "Techniques for applying, configuring, and coordinating nerve fiber stimulation," which published as US Patent Application Publication 2005/0267542

U.S. patent application Ser. No. 11/280,884, filed Nov. 15, 2005, entitled, "Techniques for nerve stimulation," which published as US Patent Application Publication 2006/0106441

U.S. patent application Ser. No. 11/340,156, filed Jan. 25, 2006, entitled, "Method to enhance progenitor or genetically-modified cell therapy," which published as US Patent Application Publication 2006/0167501

U.S. patent application Ser. No. 11/359,266, filed Feb. 21, 2006, entitled, "Parasympathetic pacing therapy during and following a medical procedure, clinical trauma or pathology," which published as US Patent Application Publication 2006/0206155

U.S. patent application Ser. No. 10/745,514, filed Dec. 29, 2003, entitled, "Nerve-branch-specific action-potential activation, inhibition, and monitoring," which published as US Patent Application Publication 2005/0149154

U.S. patent application Ser. No. 11/234,877, filed Sep. 22, 2005, entitled, "Selective nerve fiber stimulation," which published as US Patent Application Publication 2006/0100668

U.S. patent application Ser. No. 11/657,784, filed Jan. 24, 2007, entitled, "Techniques for prevention of atrial fibrillation"

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
    a monitor, configured to sense one or more physiological parameters;
    an electrode device, configured to be coupled to a baroreceptor site of a subject; and
    a control unit, configured to detect an episode of non-sinus atrial tachycardia responsively to the one or more sensed physiological parameters, and, responsively to the detection, restore normal sinus rhythm (NSR) of the subject, by:
    driving the electrode device to apply a stimulation signal to the baroreceptor site, and
    configuring the stimulation signal to lower a blood pressure of the subject sufficiently to restore the NSR.

2. The apparatus according to claim 1, wherein the non-sinus atrial tachycardia includes atrial fibrillation (AF), and wherein the control unit is configured to restore the NSR responsively to the detection of the episode of the AF.

3. The apparatus according to claim 1, wherein the non-sinus atrial tachycardia includes atrial flutter, and wherein the control unit is configured to restore the NSR responsively to the detection of the episode of the atrial flutter.

4. The apparatus according to claim 1, wherein the electrode device comprises an intravascular electrode lead.

5. The apparatus according to claim 1, wherein the control unit is configured to apply the stimulation signal at between 50 and 200 pulses per second.

6. The apparatus according to claim 1, wherein the control unit is configured to restore the NSR by:
    driving the electrode device to apply the stimulation signal at a first strength during a first stimulation session,
    determining whether the episode has been successfully resolved responsively to the one or more sensed physiological parameters, and responsively to a determination that the episode has not been resolved, driving the electrode device to apply the stimulation signal at a second strength during a second stimulation session subsequent to the first stimulation session, wherein the second strength is greater than the first strength.

7. The apparatus according to claim 1, wherein the control unit is configured to apply a cardiac muscle signal to at least one atrium of the subject selected from the group consisting of: an atrium including the atrial site, and an atrium contralateral to the atrium including the atrial site, and to configure the cardiac muscle signal to stimulate cardiac muscle tissue.

8. The apparatus according to claim 7, wherein the at least one atrium includes the atrium including the atrial site, and wherein the control unit is configured to drive the electrode device to apply the cardiac muscle signal to the atrial site.

9. The apparatus according to claim 1, wherein the control unit is configured to apply the stimulation signal during a ventricular refractory period of the cardiac cycle.

10. The apparatus according to claim 1, wherein the control unit is configured to begin to apply the stimulation signal after a delay after the detection, if the episode has not been resolved during the delay.

11. The apparatus according to claim 1, further comprising a blood pressure sensor configured to generate a blood pressure signal, wherein the control unit is configured to lower the blood pressure to a target level responsively to the blood pressure signal.

12. The apparatus according to claim 1, wherein the baroreceptor site is selected from the group consisting of: a carotid bifurcation, and a jugular vein, and wherein the electrode device is configured to be coupled to the selected site.

13. Apparatus comprising:
a monitor, configured to sense one or more physiological parameters;
an electrode device, configured to be coupled to a baroreceptor site of a subject; and
a control unit, configured to:
detect an episode of non-sinus atrial tachycardia responsively to the one or more sensed physiological parameters,
responsively to the detection, wait during a delay period,
upon conclusion of the delay period, determine whether the episode has been successfully resolved responsively to the one or more sensed physiological parameters, and
responsively to a determination that the episode has not been resolved, restore normal sinus rhythm (NSR) of the subject by:
driving the electrode device to apply a stimulation signal to the baroreceptor site, and
configuring the stimulation signal to lower a blood pressure of the subject sufficiently to restore the NSR.

14. The apparatus according to claim 13, wherein the delay period has a duration of at least ten seconds.

15. The apparatus according to claim 13, wherein the non-sinus atrial tachycardia includes atrial fibrillation (AF), and wherein the control unit is configured to restore the NSR responsively to the detection of the episode of the AF.

16. The apparatus according to claim 13, wherein the non-sinus atrial tachycardia includes atrial flutter, and wherein the control unit is configured to restore the NSR responsively to the detection of the episode of the atrial flutter.

17. The apparatus according to claim 13, further comprising a blood pressure sensor configured to generate a blood pressure signal, wherein the control unit is configured to lower the blood pressure to a target level responsively to the blood pressure signal.

18. The apparatus according to claim 13, wherein the baroreceptor site is selected from the group consisting of: a carotid bifurcation, and a jugular vein, and wherein the electrode device is configured to be coupled to the selected site.

19. A method comprising:
detecting an episode of non-sinus atrial tachycardia of a subject; and
responsively to the detecting, restoring normal sinus rhythm (NSR) of the subject, by:
applying a stimulation signal to a baroreceptor site of the subject, and
configuring the stimulation signal to lower a blood pressure of the subject sufficiently to restore the NSR.

20. The method according to claim 19, wherein the non-sinus atrial tachycardia includes atrial fibrillation (AF), and wherein detecting the episode comprises detecting the episode of the AF.

21. The method according to claim 19, wherein the non-sinus atrial tachycardia includes atrial flutter, and wherein detecting the episode comprises detecting the episode of the atrial flutter.

22. The method according to claim 19, wherein applying the stimulation signal comprises applying the stimulation signal from an intravascular site.

23. The method according to claim 19, wherein configuring the stimulation signal comprises applying the stimulation signal at between 50 and 200 pulses per second.

24. The method according to claim 19, wherein restoring the NSR comprises restoring the NSR by:
applying the stimulation signal at a first strength during a first stimulation session, and
responsively to a determination that the episode has not been resolved, applying the stimulation signal at a second strength during a second stimulation session subsequent to the first stimulation session, wherein the second strength is greater than the first strength.

25. The method according to claim 19, comprising applying a cardiac muscle signal to at least one atrium of the subject selected from the group consisting of: an atrium including the atrial site, and an atrium contralateral to the atrium including the atrial site, and configuring the cardiac muscle signal to stimulate cardiac muscle tissue.

26. The method according to claim 25, wherein the at least one atrium includes the atrium including the atrial site, and wherein applying the cardiac muscle signal comprises applying the cardiac muscle signal to the atrial site.

27. The method according to claim 19, wherein applying the stimulation signal comprises applying the stimulation signal during a ventricular refractory period of the cardiac cycle.

28. The method according to claim 19, wherein applying the stimulation signal comprises beginning to apply the stimulation signal after a delay after the detecting, if the episode has not been resolved during the delay.

29. The method according to claim 19, wherein configuring the stimulation signal comprises setting, during a calibration procedure, at least one parameter of the stimulation signal to have a minimum value sufficient to achieve a desired effect.

30. The method according to claim 29, wherein the desired effect includes a reduction in systolic blood pressure of the subject.

31. The method according to claim 19, wherein configuring the stimulation signal comprises determining, during a calibration procedure, a maximum value of at least one parameter of the stimulation signal that is safe for the subject.

32. The method according to claim 31, wherein determining the maximum value comprises determining the maximum value that does not reduce systolic blood pressure below a threshold value.

33. The method according to claim 19, comprising performing, prior to detecting the episode, an acute test to determine whether the subject is expected to benefit from the applying the stimulation signal.

34. The method according to claim 19, wherein restoring the NSR comprises:
sensing the blood pressure; and
lowering the blood pressure to a target level responsively to the sensed blood pressure.

35. The method according to claim 19, wherein the site is selected from the group consisting of: a carotid bifurcation, and a jugular vein, and applying the electrical signal comprises applying the electrical signal to the selected site.

36. A method comprising:
detecting an episode of non-sinus atrial tachycardia of a subject;
responsively to the detecting, waiting during a delay period; and
upon conclusion of the delay period, responsively to a determination that the episode has not been resolved, restoring normal sinus rhythm (NSR) of the subject by:
applying a stimulation signal to a baroreceptor site of a subject, and
configuring the stimulation signal to lower a blood pressure of the subject sufficiently to restore the NSR.

37. The method according to claim 36, wherein the delay period has a duration of at least ten seconds.

38. The method according to claim 36, wherein the non-sinus atrial tachycardia includes atrial fibrillation (AF), and wherein detecting the episode comprises detecting the episode of the AF.

39. The method according to claim 36, wherein the non-sinus atrial tachycardia includes atrial flutter, and wherein detecting the episode comprises detecting the episode of the atrial flutter.

40. The method according to claim 36, wherein restoring the NSR comprises:
sensing the blood pressure; and
lowering the blood pressure to a target level responsively to the sensed blood pressure.

41. The method according to claim 36, wherein the site is selected from the group consisting of: a carotid bifurcation, and a jugular vein, and applying the electrical signal comprises applying the electrical signal to the selected site.

* * * * *